(12) United States Patent
Mitsuhashi

(10) Patent No.: US 8,123,065 B2
(45) Date of Patent: Feb. 28, 2012

(54) CONTAINER WITH LID

(75) Inventor: Tadayoshi Mitsuhashi, Ibaraki (JP)

(73) Assignee: Prescribe Genomics Co., Ibaraki (JP)

( * ) Notice: Subject to any disclaimer, the term of this patent is extended or adjusted under 35 U.S.C. 154(b) by 1241 days.

(21) Appl. No.: 10/592,751

(22) PCT Filed: Mar. 9, 2005

(86) PCT No.: PCT/JP2005/004109
§ 371 (c)(1),
(2), (4) Date: Sep. 14, 2006

(87) PCT Pub. No.: WO2005/087603
PCT Pub. Date: Sep. 22, 2005

(65) Prior Publication Data
US 2007/0272689 A1    Nov. 29, 2007

(30) Foreign Application Priority Data

Mar. 16, 2004  (JP) .................................. 2004-075034

(51) Int. Cl.
*B65D 51/04* (2006.01)
(52) U.S. Cl. ........ 220/285; 220/200; 220/281; 220/282; 220/521; 220/810; 220/833; 220/834
(58) Field of Classification Search .................. 220/200, 220/285, 281, 282, 315, 521, 810, 833, 834; 422/102, 913
See application file for complete search history.

(56) References Cited

U.S. PATENT DOCUMENTS 1,638,837 A * 8/1927 Deitsch .......................... 190/109
(Continued)

FOREIGN PATENT DOCUMENTS

CN    1218650    10/1998
(Continued)

OTHER PUBLICATIONS

European Search Report for EP Application No. 09011569.2 mailed Nov. 27, 2009.
(Continued)

*Primary Examiner* — Anthony Stashick
*Assistant Examiner* — Elizabeth Volz
(74) *Attorney, Agent, or Firm* — Gregory B. Butler

(57) ABSTRACT

A container with a lid comprises a container portion (10) having an opening portion (11) for the loading or unloading of a sample or the like, a lid portion (20) that can be detachably fitted in said opening portion (11) so as to close the same, and a lever mechanism portion (30) for opening said lid portion (20) in a closed state using leverage. The lever mechanism portion (30) is composed of a lever portion (33) having a force-applied point (P) portion that is pressed by a finger and an action point (Q) portion that is pressed against an external periphery portion of said lid portion (20) when pressed with the finger so as to open the same, and a support portion (31, 32) for supporting said lever portion (33) via a thin-walled portion (35) that constitutes a fulcrum (O) portion, in a freely swinging manner. The lever mechanism portion (30) allows the lid portion (20) to be easily opened with one hand without putting much burden on the fingers even if it is very tightly closed. In addition, a lock mechanism portion (70) is provided that locks the lid portion (20) when it is closed. Optionally, in response to a closing operation of the lid portion (20), the lid portion (20) is automatically locked by the lock mechanism portion (70), and in response to an opening operation of the lid portion (20) by the lever mechanism portion (60), the locking of the lid portion (20) by the lock mechanism portion (70) is automatically released.

45 Claims, 12 Drawing Sheets

U.S. PATENT DOCUMENTS

| | | | | |
|---|---|---|---|---|
| 2,026,700 | A * | 1/1936 | Pearl | 220/285 |
| 3,934,722 | A * | 1/1976 | Goldberg | 206/365 |
| 5,225,165 | A | 7/1993 | Perlman | |
| 5,270,011 | A * | 12/1993 | Altherr | 422/102 |
| 5,398,837 | A | 3/1995 | Degrassi | |
| 5,863,791 | A * | 1/1999 | Baldszun et al. | 435/288.1 |
| 6,070,749 | A * | 6/2000 | Joulia | 220/4.22 |
| 6,145,688 | A | 11/2000 | Smith | |
| 6,644,492 | B1 | 11/2003 | Mitchell | |
| 2002/0088814 | A1* | 7/2002 | Belfance et al. | 220/833 |
| 2005/0061815 | A1* | 3/2005 | Wong | 220/281 |

FOREIGN PATENT DOCUMENTS

| | | |
|---|---|---|
| EP | 0 487 448 A1 | 11/1991 |
| EP | 1 153 842 A1 | 6/2000 |
| FR | 1.002.845 | 12/1949 |
| JP | 61-83546 | 11/1984 |
| JP | 4-267756 | 11/1991 |
| JP | 6-42706 | 11/1992 |
| JP | 7-167865 | 9/1994 |
| JP | 10-129697 | 11/1996 |
| JP | 10-194316 | 12/1996 |
| JP | 11-75933 | 9/1997 |
| JP | 3062266 | 3/1999 |
| JP | 2001-233367 | 2/2000 |
| JP | 2002-264959 | 3/2001 |
| WO | WO 95/09125 | 9/1993 |

OTHER PUBLICATIONS

Office Action from the Chinese Patent Office for patent application No. 2005800114054 dated on Dec. 5, 2008 in Chinese.

Supplementary European Search Report mailed Jun. 17, 2009.

International Search Report of PCT/JP2005/004109 mailed Jun. 21, 2005.

JPO Office Action Notice of Rejection mailed Aug. 14, 2007, in Japanese.

* cited by examiner

CONTAINER WITH LID

TECHNICAL FIELD

The present invention relates to a container with a lid, such as a sample tube for the storage of a sample or the like, the container with a lid consisting of a container portion with an opening portion for the loading and unloading of a sample or the like, and a lid portion that can be detachably fitted with the opening portion so as to close the same.

BACKGROUND ART

A conventional example of the aforementioned type of a container with a lid is shown in FIG. 12. FIG. 12(A) is a plan view, and FIG. 12(B) is a sagittal cross section taken along V-V of FIG. 12(A). A container 100 with a lid shown is a container generally referred to as a sample tube with a height of about 4 cm and a diameter of about 1 cm. It is used for the storage, mixture, centrifugation or the like of a sample or the like in biology laboratories, for example. It includes a container portion 10 with an opening portion 11 for the loading and unloading of a content such as a sample, and a lid portion 20 that can be detachably fitted with the opening portion 11 (upper-end portion of container portion 10) so as to close the same.

More specifically, the container portion 10 is cylindrical in shape in the upper portion thereof. Its lower portion, which is not shown, is conically shaped, as shown in FIG. 1(B). The container portion 10 is either transparent or semi-transparent. Along the outer periphery of the container portion 10 near the upper end thereof, a flange portion 15 is integrally provided for reinforcement and for functioning as a lid receiver. The flange portion 15 and the lid portion 20 are coupled by means of a flexible sheet hinge portion 25.

The lid portion 20 includes a lid-body portion 21 with an inverted-U cross section that is externally fitted with an upper-end portion (opening portion 11) of the container 10. It also includes an internally fit portion 22 with a short-cylinder shape that is hermetically and internally fitted with the upper end portion (opening portion 11) of the container 10. It is also provided with a protruding nail portion 27 protruding from the lid-body portion 21 outwardly in the radial direction (in the plane of the opening of the container portion 10 and beyond the flange portion 15), thus providing a finger rest for opening the lid portion 20.

The container portion 10, the flange portion 15, the hinge portion 25, and the lid portion 20, of which the container with a lid 100 is composed, are all formed of the same synthetic resin material.

In the thus-structured container with a lid 100, when opening the lid portion 20 from the closed state shown in (B), the protruding nail portion 27 is pushed or pulled up with a finger, whereby the lid portion 20 can be opened as shown in (C). Conversely, when closing it from the open state (C), the lid portion 20 is placed on the opening portion 11 of the container portion 10 and pushed down. As a result, as shown in (B), the internally fit portion 22 is pressed within the internal periphery of the opening portion 11, whereby the opening portion 11 is hermetically closed.

Although large force must be initially applied when opening the lid portion 20, the lid can be fully opened easily once it is even slightly moved in the opening direction.

However, in the conventional container with a lid (sample tube) 100, once a sample or the like is put in the container portion and stored as frozen or refrigerated with the lid portion closed, it has often been difficult to open the lid portion so as to use the stored sample for experiment or measurement, for example, when the lid portion is very tightly closed.

If the lid portion cannot be easily opened, a tremendous amount of time and energy would have to be spent for opening and closing the lid portion if hundreds of sample tubes are involved. That would hinder the necessary experiment or measurement, and could possibly hurt the fingers due to the large burden placed on them.

Further, when the sample needs to be sucked out with a pipette, for example, if the lid portion is too tightly closed, it would be impossible to open the lid portion with a single hand. As a result, it would be necessary, for example, to once place the pipette held in the right hand on the experiment table or the like, hold the sample tube with the left hand, and then open the lid portion, with some difficulty, with the right hand. This would result in a greatly reduced efficiency and a longer time for the pipetting of the sample. Even if the time loss per single instance of opening or closing is small, the total time loss cannot be ignored when the lid portion needs to be opened or closed thousands or tens of thousands of times.

On the other hand, in the conventional sample tube, the lid portion supposed to be tightly closed could inadvertently be opened. Specifically, sometimes it is necessary to heat the sample tube containing a sample when subjecting the sample to an experiment or measurement. In such a case, the portion of the sample tube below its upper portion (lid portion) is submerged in a hot water bath so as to heat the sample in a cyclic movement, when the pressure inside the sample tube could increase so much that the lid portion is opened. If that happens, splashes of the hot water, the surface of which is agitated by the cyclic movement in the sample tube, could jump into the sample tube, thereby completely ruining the sample.

In order to prevent such a problem, conventionally the lid portion is locked by means of a separate clip or the like that is attached between the lid portion and the container portion, thereby preventing the accidental opening of the lid portion. However, when the lid portion is locked by a separate clip or the like, the clip or the like needs to be locked and unlocked for opening and closing the lid portion, which is troublesome and time-wasting.

It is therefore an object of the invention to solve the aforementioned problems and to provide a container with a lid in which the lid portion can be easily opened with one hand without placing too much burden on the fingers even if it is tightly closed, and which container has a relatively simple structure and can be manufactured at low cost.

Another object of the invention is to provide a container with a lid that can be locked so that the lid portion does not open inadvertently due to the increase in the internal pressure, for example, in which the locking and unlocking operations can be very simply carried out, and which has a relatively simple structure and can be manufactured at low cost.

It is yet another object of the invention to provide a container with a lid whereby the aforementioned two objects can be achieved simultaneously and reasonably.

DISCLOSURE OF THE INVENTION

In order to achieve the aforementioned objects, the invention provides, in a first embodiment, a container with a lid comprising a container portion having an opening portion for loading and unloading a content such as a sample, and a lid portion that can be detachably fitted in said opening portion so as to close the same. The container, which can be used as a sample tube, for example, further comprises a lever mechanism portion for opening said lid portion when said opening portion is closed thereby, using leverage.

In a second embodiment, the invention provides a container with a lid comprising: a container portion having an opening portion for loading and unloading a content such as a sample; a lid portion that can be detachably fitted in said opening portion so as to close the same; and a lock mechanism portion integrally provided with said container portion and/or said lid portion so as to lock said lid portion when said opening portion is closed thereby.

In a third embodiment, the invention provides a container with a lid comprising: a container portion having an opening portion for loading and unloading a content such as a sample; a lid portion that can be detachably fitted in said opening portion so as to close the same; a lever mechanism portion for opening said lid when said opening portion is closed thereby, using leverage; and a lock mechanism portion integrally provided with said container portion and/or said lid portion so as to lock said lid portion when said opening portion is closed thereby.

The lever mechanism portion provided in the container with a lid in the first embodiment functions as an opener. In a preferred embodiment, it is composed of a lever portion having a force-applied point where finger pressure is applied and an action point that is pressed against an external periphery portion of said lid portion so as to open the same, and a support portion that supports said lever portion via a fulcrum portion in a freely swinging manner.

The lever mechanism portion may be of a rotary type in which the fulcrum portion is located between said force-applied point portion and said action point portion in said lever portion. Alternatively, it may be of a push-up type in which the action point portion is located between said force-applied point portion and said fulcrum portion in said lever portion.

In another preferred embodiment, the lever portion and said support portion of said lever mechanism portion are continuous via a flexible thin-walled portion and that constitutes said fulcrum portion. In this case, preferably the thin-walled portion comprises a groove having a circular or triangular cross section on the internal surface thereof.

In a more preferable embodiment, the support portion of said lever mechanism portion includes a pair of left and right support piece portions protruding, with a predetermined interval provided therebetween, in a direction along the plane of the opening of said container portion, wherein said lever portion is disposed between said pair of support piece portions, and wherein said pair of support piece portions are connected to the force-applied-point side portion of said lever portion via a thin-walled portion that constitutes said fulcrum portion.

At least the thin-walled portion is made such that it has an appropriate level of resilience. In this way, the lever portion returns to the original position (such as a horizontal position) as the hand is released from the lever portion after the lid portion is opened, such that it does not pose an obstacle when closing the lid, for example.

Preferably, the lid portion includes a protruding nail portion against which the action point of said lever portion is pressed and that protrude in a direction along the plane of the opening of said container portion.

In another preferred embodiment, the lid portion includes a lever swinging convex portion that presses the action point of said lever portion downward when said lid portion is closed. In this way, when the lid is closed, it becomes possible to cause portion of the lever portion toward the force-applied point (one end) to be swung upward above the fulcrum portion when the lid is closed. As a result, the length that the lever portion protrudes laterally (in the horizontal direction) when the lid is closed can be reduced while a desired leverage ratio is maintained, so that the space occupied by the container with a lid (particularly in a plan view) can be reduced.

In another preferred embodiment, a finger-pressed convex portion is provided at a force-applied point portion of said lever portion that is pressed by a finger. In this way, the lid-opening operation by the lever mechanism portion can be even more facilitated.

The container portion, the lid portion, and the lever mechanism portion may be all formed integrally from the same material, whereby the manufacturing cost can be reduced. However, this is merely an example, and the individual portions may be separately provided. Particularly, at least the lever portion of the lever mechanism portion may be provided separately from the other members.

Thus, in the container with a lid according to the first embodiment of the invention that is equipped with the lever mechanism portion (opener), when opening the lid portion, the container portion is held with one hand, and one end (force-applied point portion) of the lever portion of the lever mechanism portion is pressed with the thumb of the one hand. As a result, the pressing force is increased in accordance with the leverage ratio (ratio of the length between the fulcrum and the force-applied point to the length between the fulcrum and the action point) when it acts on the lid. Thus, the lid portion can be easily opened without putting much burden on the fingers even if the lid portion is very tightly closed, thereby enhancing its utility and product value greatly.

Preferably, the lock mechanism portion provided in the container with a lid according to the second embodiment is composed of a first locking portion provided on one of said container portion or said lid portion, and a second locking portion provided on a locking hinge portion integrally formed with the other of said container portion and said lid portion, wherein said second locking portion engages said first locking portion.

In this case, in a preferred embodiment, at least one of said first locking portion and said second locking portion engages the other by elastically deforming when one side of said locking hinge portion is swung toward said first locking portion. In a more preferable embodiment, the first locking portion is spherical in shape, and said second locking portion comprises a concave portion having a spherical surface in which said first locking portion is fitted.

Thus, in the container with a lid according to the second embodiment in which the lock mechanism portion is integrally provided, when locking the lid portion in a closed state, the container portion is held with one hand and one side of the locking hinge portion on which the second locking portion is provided is caused to swing toward the first locking portion side with a finger of the one hand (or the other hand). As a result, for example, at least one of the first locking portion and the second locking portion elastically deforms and the second locking portion engages the first locking portion, whereby the lid portion is locked. When thus locked, the lid portion is prevented from being inadvertently opened by, for example, an increase in the internal pressure of the container with a lid. In order to unlock the lock mechanism portion when opening the lid portion, one side of the locking hinge portion on which the second locking portion is provided only needs to be caused to swing in the opposite direction from when locking the lid portion, namely, in a direction away from the first locking portion.

Thus, in the container with a lid equipped with the lock mechanism portion according to the invention, because the lock mechanism portion is integrally provided with the container portion and/or the lid portion, the locking and unlocking operation of the lid portion can be more easily carried out than when the lid portion is locked with a clip or the like as is conventional.

Meanwhile, in the container with a lid according to the third embodiment that is equipped with both the lever mechanism portion (opener) and the lock mechanism portion, preferably the lever mechanism portion and the lock mechanism portion are operatively linked.

In a more preferable embodiment, in response to a closing operation of the lid portion, the lid portion is locked by the lock mechanism portion, and in response to an opening operation of the lid portion by the lever mechanism portion, the locking of the lid portion by the lock mechanism portion is released.

In a more preferable embodiment, the lever mechanism portion includes a lever portion having a force-applied point portion that is pressed with a finger and an action point that is pressed against an external periphery portion of said lid portion so as to open the same, and a support portion that supports said lever portion via said fulcrum portion in a freely swinging manner, wherein said lever portion and said support portion are continuous via a thin-walled portion that constitutes said fulcrum portion and that is flexible, said lever portion and said support portion forming a leverage/locking hinge portion, and wherein said lock mechanism portion is composed of a first locking portion provided on said lid portion, and a second locking portion provided on said leverage/locking hinge portion toward said lever portion, said second locking portion engaging said first locking portion.

In a preferred embodiment, the first locking portion of said lock mechanism portion is spherical in shape, wherein said second locking portion comprises a concave portion having a spherical surface in which said first locking portion can be fitted, and wherein at least one of said first locking portion and said second locking portion engages the other by elastically deforming upon closing of said lid portion. Preferably, said lid portion is provided with a lever swinging convex portion that presses the action point portion of said lever portion downward when said lid portion is closed.

Thus, in the container with a lid according to the third embodiment that is equipped with the lever mechanism portion and the lock mechanism portion, when opening the lid portion, the container portion is held with one hand, and one end (force-applied point portion) of the lever portion (leverage/locking hinge portion) of the lever mechanism portion is pressed with the thumb of the one hand. As a result, the pressing force is increased in accordance with the leverage ratio when it acts on the lid portion. Thus, the lid portion can be opened with one hand easily without putting much burden on the fingers even if the lid portion is closed very tightly. In this case, in a preferred embodiment, the lever mechanism portion and the lock mechanism portion are operatively linked with each other. Specifically, in response to an opening operation of the lid portion by the lever mechanism portion, the locking of the lid portion by the lock mechanism portion is automatically released.

In order to lock the lid portion, for example, the container portion is held with one hand, and the lid portion is closed with the fingers of the one hand (or the other hand). In operative linkage therewith, namely, in response to the closing operation of the lid portion, the lever portion (one side of the leverage/locking hinge portion) of the lever mechanism portion is caused to swing in the opposite direction from when the lid portion is opened. As a result, at least one of the first locking portion and the second locking portion elastically deforms and the first locking portion and the second locking portion engage with each other. Thus, the lid portion is automatically locked and is prevented from being inadvertently opened by an increase in the internal pressure or the like.

Thus, in accordance with the container with a lid equipped with the lever mechanism portion and the lock mechanism portion according to the invention, the locking and unlocking operations can be performed automatically in operative linkage with the closing operation of the lid portion or the opening operation of the lid portion by the lever mechanism portion. Accordingly, as compared with the conventional example in which the lid portion is locked with a separate clip or the like, the locking and unlocking operations can be very easily and reliably carried out.

In addition to the foregoing, because the lever mechanism portion and/or the lock mechanism portion have such a relatively simple structure that they can be integrally formed with the other members, the container with a lid as a whole can be manufactured at approximately the same cost as is conventional.

In the container with a lid according to any of the foregoing embodiments, the lid portion is connected with said container portion via a lid hinge portion in a freely swinging manner.

The lid hinge portion comprises a flexible sheet or wire member, or a plate member having a thin-walled portion, any of which member is integrally formed with said lid portion and said container portion.

The lid hinge portion comprising said plate member is composed of a first plate hinge portion and a second plate hinge portion that are formed side by side, wherein said first plate hinge portion has a thin-walled bending portion formed near the center thereof, said thin-walled bending portion comprising a groove that opens downwardly, and wherein said second plate hinge portion has a ridge portion formed near the center thereof which protrudes upwardly, wherein said thin-walled bending portion is formed on the left and right sides of said ridge portion.

Preferably, the lid hinge portion has an appropriate level of resilience.

In a more preferable embodiment, the container portion is cylindrical in shape at least in an upper portion thereof and is of such a size that it can be held with one hand.

While the container with a lid according to the invention is most suitable for a sample tube for the storage of a sample or the like, this is merely an example and it can be used as a container for the storage of various kinds of liquid, powder and the like, such as shampoo, soy sauce, salt, pepper and other condiments.

The container with a lid according to the invention can be made of one or a plurality of kinds of materials from synthetic resin, metal, glass, ceramic, and a composite material thereof. In this case, when the individual portions are separate, different materials may be used therefor (namely, the lever portion may be made of metal and the other portions may be made of synthetic resin, for example).

In another preferred embodiment of the invention, the container portion and the other portions are separate.

In this case, the portions other than the container portion are made in the form of a detachable lid portion that can be detachably attached to the container portion. In a more preferable embodiment, the detachable lid portion is integrally provided with the lid portion, the lever mechanism portion, and/or the lock mechanism portion.

In an example of the configuration for detachably attaching the detachable lid portion to the container portion, a male or female screw portion is provided at an upper part of the container portion, and a female or male screw portion that threadedly engages the male or female screw is provided on the detachable lid portion.

Thus, by constructing the container with a lid with a container portion and a detachable lid portion that can be detachably attached to each other, the detachable lid portion and the container portion can be made of different materials, thereby increasing the degree of freedom in the choice of material.

Furthermore, by preparing a plurality of types of detachable lid portions with different structures in the lever mechanism portion or the lock mechanism portion that can be detachably attached to the container portion, it becomes possible to select one that is most suitable for the type of the stored item, such as a sample, or the environment in which it is stored. In addition, because the container portion can be used in common, an increase in product value and cost reduction can be achieve, as compared with a case where a plurality of types of containers with a lid consisting of a container and other portions that are integrally formed therewith are manufactured.

BRIEF DESCRIPTION OF THE DRAWINGS

FIG. 1(A) is a plan view showing an open lid portion and FIG. 1(B) is a lateral view of (A).

FIG. 3(A) is a plan view showing a closed lid portion. FIG. 3(B) shows a Y-Y sagittal cross section of (A). FIG. 3(C) shows a cross section illustrating the lid portion being opened from the state (B).

FIG. 4(A) shows a plan view of a closed lid portion. FIG. 4(B) shows a Z-Z sagittal cross section of (A). FIG. 4(C) shows a cross section illustrating the lid portion being opened from the state (B).

FIG. 5 shows a container with a lid according to a fourth embodiment of the invention.

FIG. 10(A) is a perspective view showing an open lid portion. FIG. 10(B) is a cross section showing a closed lid portion.

FIG. 11(A) shows the container with a lid, which consists of a detachable lid member and a container portion, in which the detachable lid member has been removed from the container portion. FIG. 11(B) shows the detachable lid member of (A) as attached to the container portion.

FIG. 1(B) shows a V-V sagittal cross section of (A).

BEST MODES FOR CARRYING OUT THE INVENTION

Embodiments of the container with a lid according to the invention will be hereafter described with reference to the drawings.

First Embodiment

Figure 1:
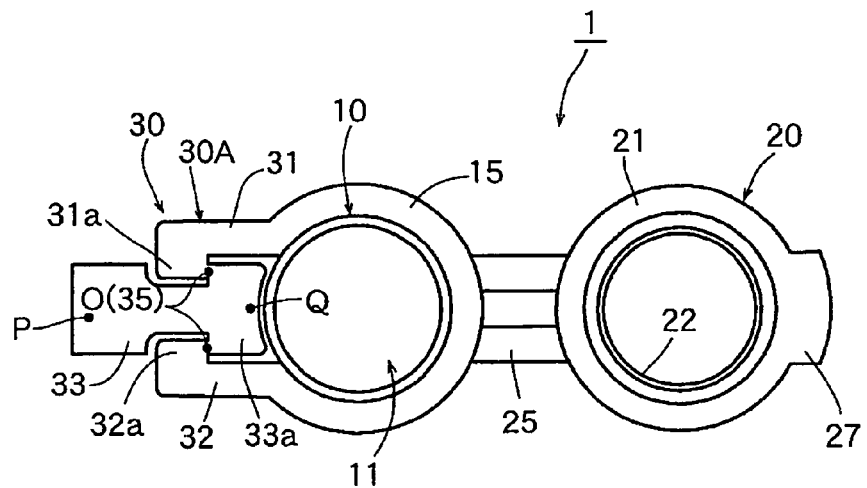
FIG. 1 shows a container with a lid according to a first embodiment of the invention.
Figure 1:
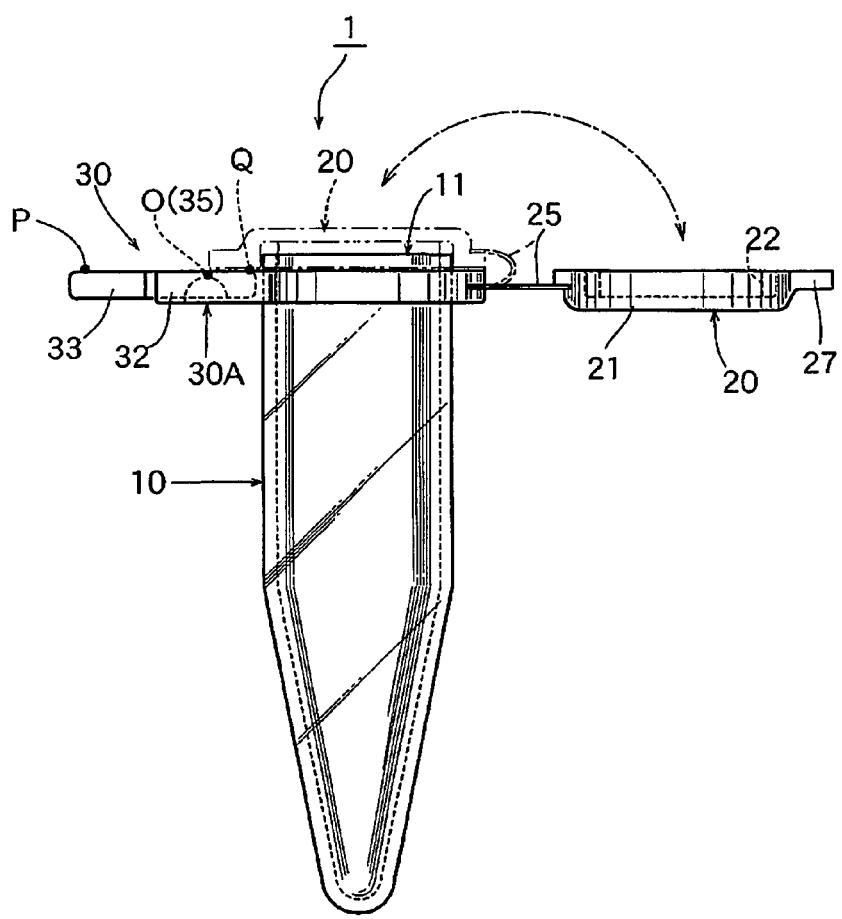

FIG. 1 shows a first embodiment of the container with a lid according to the invention. FIG. 1(A) shows a plan view of the container with the lid portion completely opened. FIG. 1(B) shows a side view. In FIG. 1, parts corresponding to the parts of the container with a lid 100 according to the conventional example shown in FIG. 12 are designated with similar numerals (throughout FIGS. 2 to 11 as well, which will be referred to later).

Figure 12:
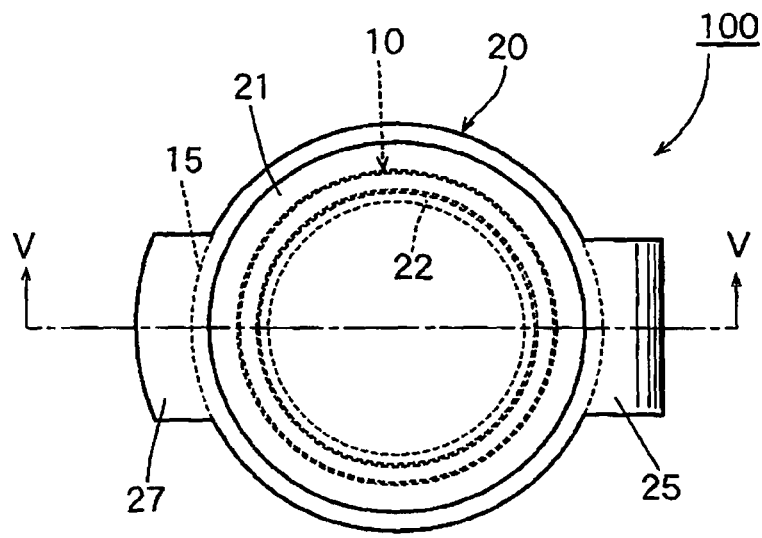
FIG. 12(A) shows a plan view of a conventional container with a lid, in which the lid portion is closed.
FIG. 12(C) shows a cross section illustrating the lid portion being opened from the state (B).
Figure 12:
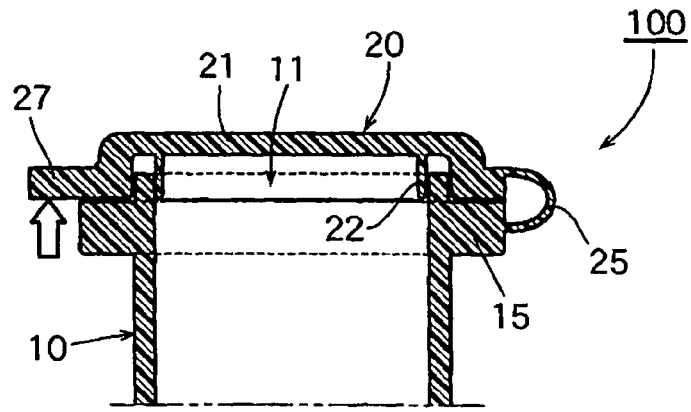
Figure 12:
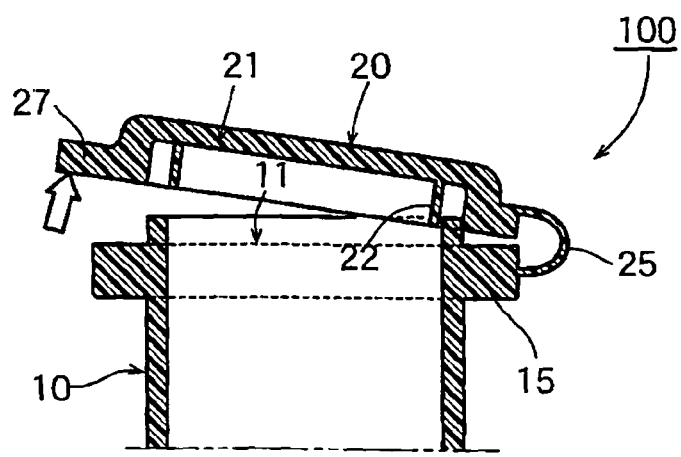

The container with a lid 1 according to the present embodiment, as in the one shown in FIG. 12, is a sample tube with a height of about 4 cm and a diameter of about 1 cm which is used for the storage, mixing, or centrifugation, for example, of a sample or the like in biology laboratories or the like. The container with a lid 1 includes a container portion 10 with an opening portion 11 for the loading and unloading of a content such as a sample, and a lid portion 20 that is detachably fitted with the opening portion 11 (upper-end portion of the container portion 10) so as to close the same. In addition, the container includes a lever mechanism portion 30 for opening the lid portion 20 when the opening portion 11 is closed thereby, using leverage.

Figure 2:
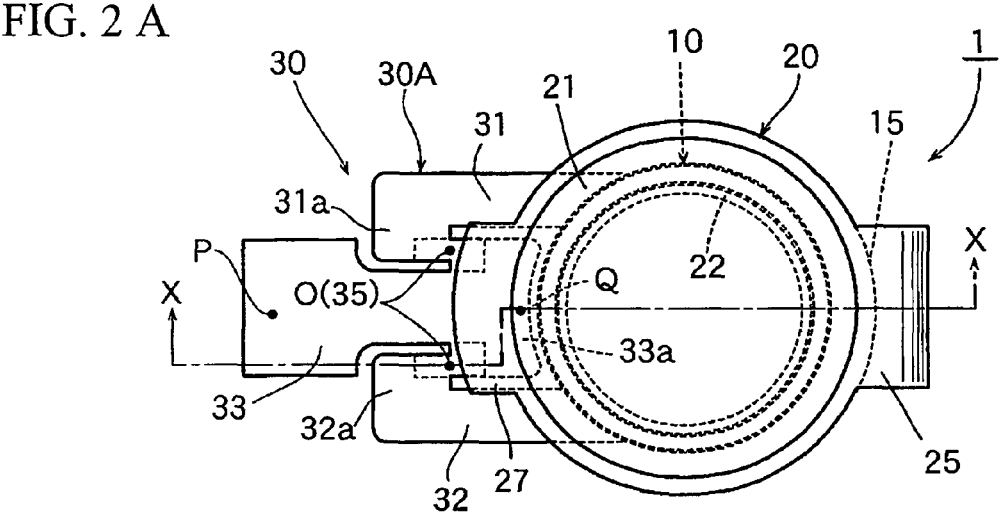
FIG. 2(A) shows a plan view of the container with a lid according to the first embodiment in which the lid portion is closed.
FIG. 2(B) shows an X-X sagittal cross section.
FIG. 2(C) shows a plan view showing the lid portion being opened from the state (B).
Figure 2:
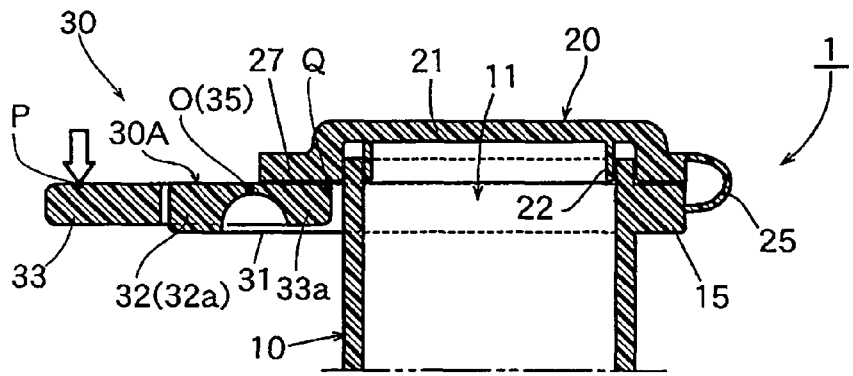
Figure 2:
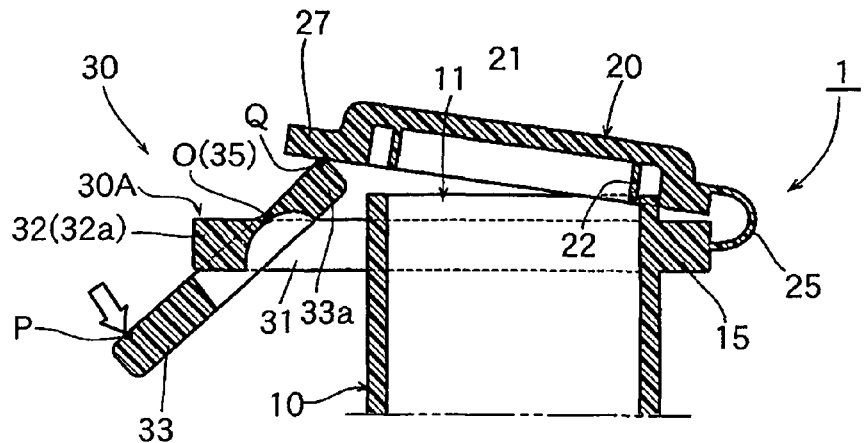

More specifically, the container portion 10, which is transparent or semi-transparent, is cylindrical in shape in the upper portion thereof and conical in the lower portion thereof. Along the outer periphery of the container portion 10 near the upper end thereof, a flange portion 15 is integrally provided. This will be more readily understood by referring to FIG. 2 in addition to FIG. 1, FIG. 2(A) showing the container with the lid portion 20 closed and FIG. 2(B) showing an X-X sagittal cross section of the container (only the upper portion thereof). The flange portion 15, which serves both as a reinforcement and a lid receiver and which is partially cut out as seen in a plan view, is connected with the lid portion 20 via a flexible sheet hinge portion 25.

The lid portion 20 includes a lid-body portion 21 which is inversely U-shaped in cross section and which is externally fitted with the upper-end portion (opening portion 11) of the container portion 10. It also includes an internally fit portion 22 with a short-cylinder shape that is hermetically internally fitted with the upper-end portion (opening portion 11) of the container portion 10. It further includes a protruding nail portion 27 used for the opening and closing of the lid portion 20 which protrudes from the lid-body portion 21 outwardly in the radial direction (in the plane of the opening of the container portion 10 and laterally beyond the flange portion 15).

The lever mechanism portion 30 is composed of a lever portion 33 having a portion constituting a force-applied point P where finger pressure is applied and a portion constituting an action point Q that is pressed against the lower surface of the protruding nail portion 27 when opening the lid portion 20, and a support portion 30A (31, 32) that is continuous with the flange portion 15 and which supports the lever portion 33 via a fulcrum O in a freely swinging manner.

More specifically, the support portion 30A of the lever mechanism portion 30 includes a pair of left and right support piece portions 31 and 32 that are L-shaped in a plan view and that protrude, with a predetermined interval provided therebetween, in a direction along the plane of the opening of the container portion 10 (radial direction). Between the pair of support piece portions 31 and 32, a lever portion 33 that has a portion that is T-shaped in a plan view (overall, it is in the shape of I or the Roman numeral of 1 in a plan view) is disposed. The support portion 30A is continuous with the lever portion 33 via a thin-walled portion 35 that has flexibility and appropriate resilience, where the fulcrum portions O are constituted by lower side portions 31a and 32a of the pair of left and right support piece portions 31 and 32 and the left and right edges of an upper side portion 33a of the lever portion 33. The internal periphery surface of the thin-walled portion 35 is formed with a groove having a semi-circular cross section.

Thus, the lever mechanism portion 30 of the present embodiment is of a rotating type where the fulcrum portions O are located between the force-applied point P and the action point Q.

The individual members of the container with a lid 1 of the present embodiment, namely, the container portion 10, the lid portion 20, the flange portion 15, the lever mechanism portion 30 (support portion 30A and lever portion 33), the hinge portion 25, and the protruding nail portion 27 are all integrally formed from the same material, which is a synthetic resin.

In such container with a lid 1, when opening the lid portion 20 from the closed state shown in FIG. 2(B), the container portion 10 is held with one hand, and one end of the lever portion 33 of the lever mechanism portion 30 is pushed down at the upper surface thereof with the thumb of the same hand (force-applied point P). As a result, as shown in FIG. 2(C), the one end of the lever portion 33 (force-applied point P) is pushed down via the fulcrum O in the (center of) the thin-walled portion 35 (namely, by the elastic deformation of the thin-walled portion 35). At the same time, the other end of the lever portion 33 (upper side portion 33a) rises whereby the action point Q on the upper surface thereof presses the lower surface of the protruding nail portion 27 so as to raise the same, thereby opening the lid portion 20.

When opening the lid portion 20, although a large force is required at the beginning, it can be fully opened easily once it is moved even a little in the opening direction.

In this case, as the one end (force-applied point P) of the lever portion 33 of the lever mechanism portion 30 is pushed, the pushing force is increased in accordance with the leverage ratio (ratio of the length between fulcrum O and force-applied point P to the length between fulcrum O and action point Q) when it acts on the lid portion 20 (protruding nail portion 27). Thus, even if the lid portion 20 is tightly closed, it can be easily opened with one hand without putting too much burden on the fingers. As a result, the container becomes more convenient and its product value greatly increases.

Furthermore, as the lever mechanism portion 30 has a relatively simple structure in which it is integrally formed with the other members, the container with a lid 1 as a whole can be manufactured at a cost not much different from that of conventional products.

When closing the lid portion 20 from an open state, the lid portion 20 is placed on the opening portion 11 of the container portion 10 and pressed downward, as in conventional examples.

Because the thin-walled portion 35 has appropriate resilience, the lever portion 33 returns to its original position (horizontal position) when, after the lid portion 20 is opened, the user releases his or her hand from the lever portion 33, thus presenting no obstacle when closing the lid portion 20, for example.

Second Embodiment

Figure 3:
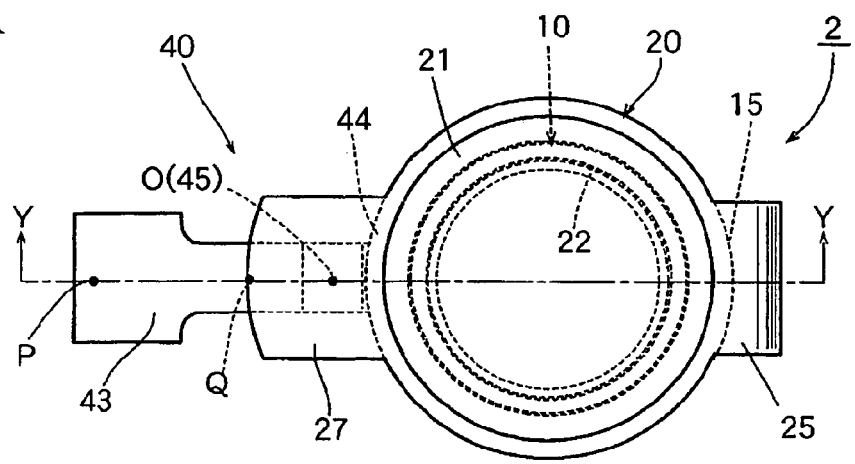
FIG. 3 shows a container with a lid according to a second embodiment of the invention.
Figure 3:
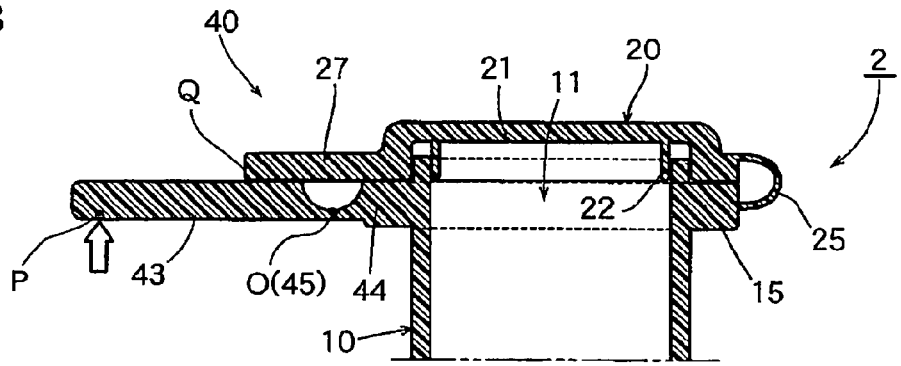
Figure 3:
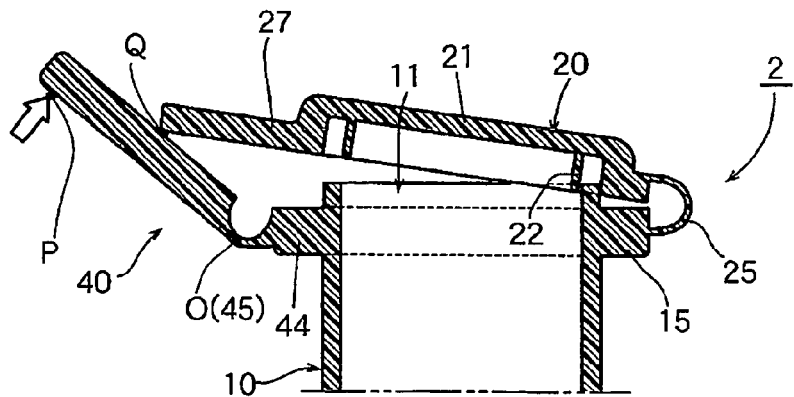

FIG. 3 shows a second embodiment of the container with a lid of the invention. FIG. 3(A) shows a plan view with the lid portion 20 closed, and FIG. 3(B) shows a Y-Y sagittal cross section of FIG. 3(A).

The container with a lid 2 according to the present embodiment is similar to the container with a lid 1 according to the first embodiment, with the only difference lying in the structure of the lever mechanism portion. Since the other portions (container portion 10, lid portion 20, and so on) are substantially identical, attention is focused on the lever mechanism portion 40 in the following description.

The lever mechanism portion 40 according to the present embodiment includes a lever portion 43 having a force-applied point portion P which is pressed by a finger and an action point portion Q that is pressed against the lower surface of one end of the protruding nail portion 27 so as to open the lid portion 20. The lever mechanism portion 40 also includes a support portion 44 for supporting the lever portion 43 via a thin-walled portion 45 constituting a fulcrum O in a freely swinging manner. The support portion 44 is formed by a part of the flange portion 15. The thin-walled portion 45 is formed with a groove with a semi-circular cross section in the internal peripheral surface thereof and it has flexibility and appropriate resilience.

Thus, the lever mechanism portion 40 according to the present embodiment is of a push-up type wherein the action point Q exists between the force-applied point P and the fulcrum O in the lever portion 43.

In the container with a lid 2 according to the second embodiment, the individual members, namely, the container portion 10, the lid portion 20, the flange portion 15, the lever mechanism portion 40 (support portion 44 and lever portion 43), the hinge portion 25, and the protruding nail portion 27 are all integrally formed from the same material, which is a synthetic resin.

In the thus structured container with a lid 2, when opening the lid portion 20 from the closed state shown in FIG. 3(B), the container portion 10 is held with one hand, and the lower surface of one end of the lever portion 43 (force-applied point P) of the lever mechanism portion 40 is pressed upward with the thumb of the same hand. As a result, as shown in FIG. 3(C), the one end of the lever portion 43 (force-applied point P) is pressed upward via the fulcrum O at (the center of) the thin-walled portion 45 (by the elastic deformation of the thin-walled portion 45). At the same time, the action point Q, which is located between the force-applied point P and the fulcrum O in the lever portion 43, presses against the lower surface of the one end of the protruding nail portion 27, whereby the one end is raised and the lid portion 20 is opened.

Although a large force is required initially when opening the lid portion 20, the lid portion can be opened easily once it is even a little moved in the opening direction.

In this case, as the one end (force-applied point P) of the lever portion 43 of the lever mechanism portion 30 is pushed, the pushing force is increased in accordance with the leverage ratio (ratio of the length between fulcrum O and force-applied point P to the length between fulcrum O and action point Q) when it acts on the lid portion 20 (protruding nail portion 27). Thus, even if the lid portion 20 is tightly closed, it can be easily opened with one hand without putting too much burden on the fingers. As a result, the container becomes more convenient and its product value greatly increases.

Furthermore, as the lever mechanism portion 40 has a relatively simple structure in which it is integrally formed with the other members, the container with a lid 2 as a whole can be manufactured at a cost not much different from that of conventional products.

Third Embodiment

Figure 4:
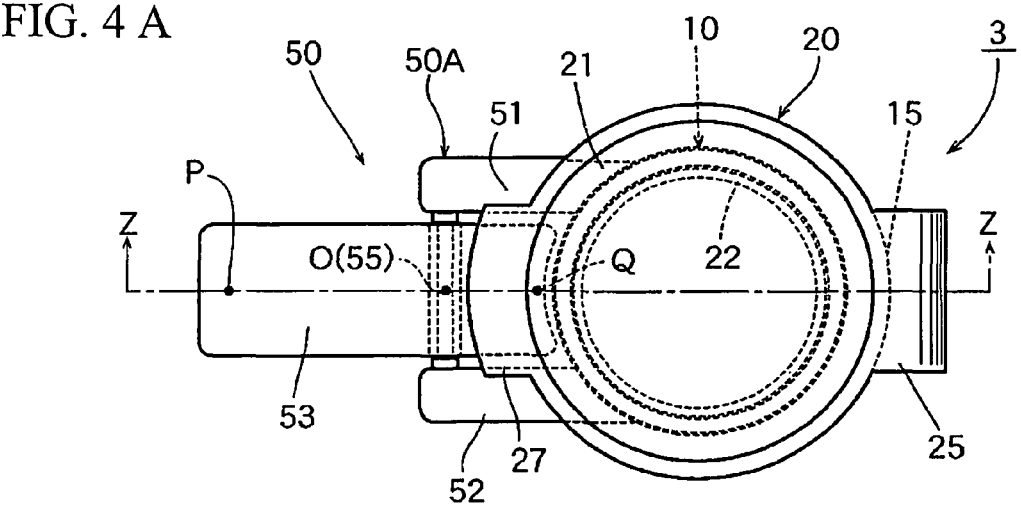
FIG. 4 shows a container with a lid according to a third embodiment of the invention.
Figure 4:
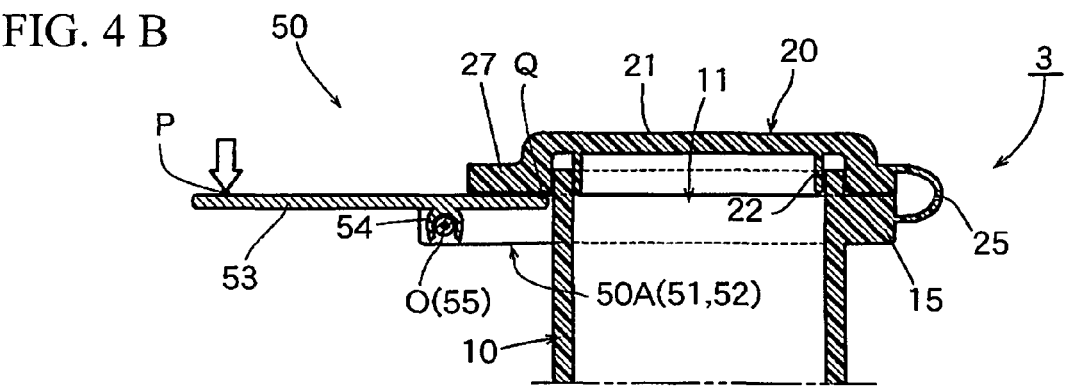
Figure 4:
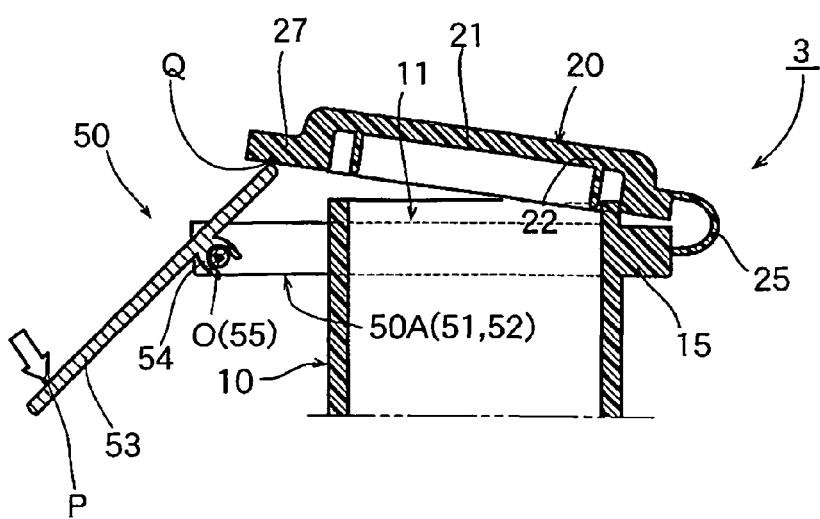

FIG. 4 shows a third embodiment of the container with a lid of the invention. FIG. 4(A) shows a plan view with the lid portion 20 closed, and FIG. 4(B) shows a Z-Z sagittal cross section of FIG. 4(A).

The container with a lid 3 according to the present embodiment is similar to the container with a lid 1 according to the first embodiment, with the only difference lying in the structure of the lever mechanism portion. Since the other portions (container portion 10, lid portion 20, and so on) are substantially identical, attention is focused on the lever mechanism portion 50 in the following description.

The lever mechanism portion 50 according to the present embodiment includes a lever portion 53 having a force-applied point portion P that is pressed with a finger and an action point portion Q that is pressed against the lower surface of the protruding nail portion 27 so as to open the lid portion 20. The lever mechanism portion 50 also includes a support portion 50A (51, 52) that is continuous with the flange portion 15 for supporting the lever portion 53 via a support shaft portion 55 constituting the fulcrum O, in a freely swinging manner.

More specifically, the support portion 50A of the lever mechanism portion 50 includes a pair of left and right support piece portions 51 and 52 that protrude, with a predetermined interval provided therebetween, in a direction along the plane of the opening of the container portion 10 (radial direction). A support shaft portion 55 is horizontally and integrally formed with the support piece portions such that it bridges between one edges of the pair of support piece portions 51 and 52.

The lever portion 53 is rectangular in shape, on the lower surface of which a C-shaped externally fit portion 54 is integrally provided which is externally and rotatably fit on the support shaft portion 55 with an appropriate snapping force. The lever portion 53 is separate from the support piece portions 51 and 52 as well as the support shaft portion 55. It is made of a material having a greater rigidity than that of these other portions.

The lever mechanism portion 50 according to the present embodiment is of a rotating type, as in the first embodiment, such that the fulcrum O exists between the force-applied point P and the action point Q in the lever portion 53.

In the container with a lid 3 of the present embodiment, the individual portions of the lever mechanism portion 50 other than the lever portion 53, namely, the container portion 10, the lid portion 20, the flange portion 15, the support portion 50A (51, 52) of the lever mechanism portion 50, the support shaft portion 55, the hinge portion 25, and the protruding nail portion 27, are integrally formed from the same material, as in the first embodiment. Namely, the material is a synthetic resin.

In the thus structured container with a lid 3, too, when opening the lid portion 20 from the closed state shown in FIG. 4(B), the container portion 10 is held with one hand, and one end of the lever portion 53 of the lever mechanism portion 50 is pushed down on the upper surface thereof (force-applied point P) with the thumb of the one hand. As a result, as shown in FIG. 4(C), the one end of the lever portion 53 (force-applied point P) is pushed down via the support shaft portion 55 as a fulcrum O. At the same time, the action point portion Q on the other end of the lever portion 53 presses against the lower surface of the protruding nail portion 27, whereby the protruding nail portion 27 is raised and the lid portion 20 is opened.

When opening the lid portion 20, a large force is required initially, but the lid portion can be easily and fully opened once it is even a little moved in the opening direction.

In this case, as the one end (force-applied point portion P) of the lever portion 53 of the lever mechanism portion 50 is pushed, the pushing force is increased in accordance with the leverage ratio (ratio of the length between fulcrum O and force-applied point P to the length between fulcrum O and action point Q) when it acts on the lid portion 20 (protruding nail portion 27). Thus, even if the lid portion 20 is tightly closed, it can be easily opened with one hand without putting too much burden on the fingers. As a result, the container becomes more convenient and its product value greatly increases.

Fourth Embodiment

Figure 5A:
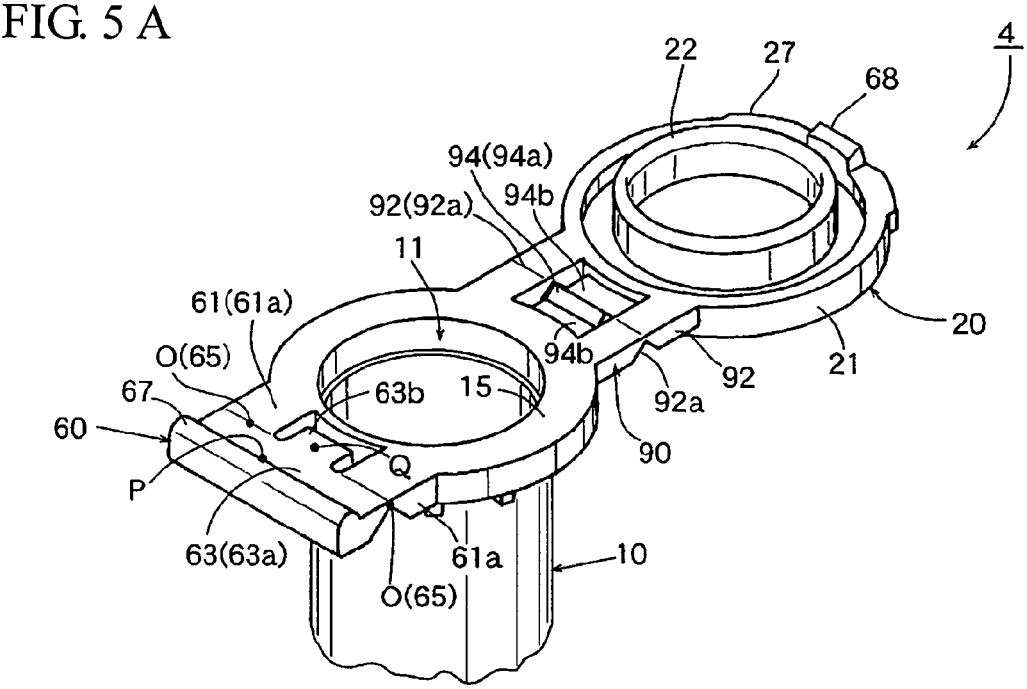
FIG. 5(A) shows a perspective view of an open lid portion.
Figure 5B:
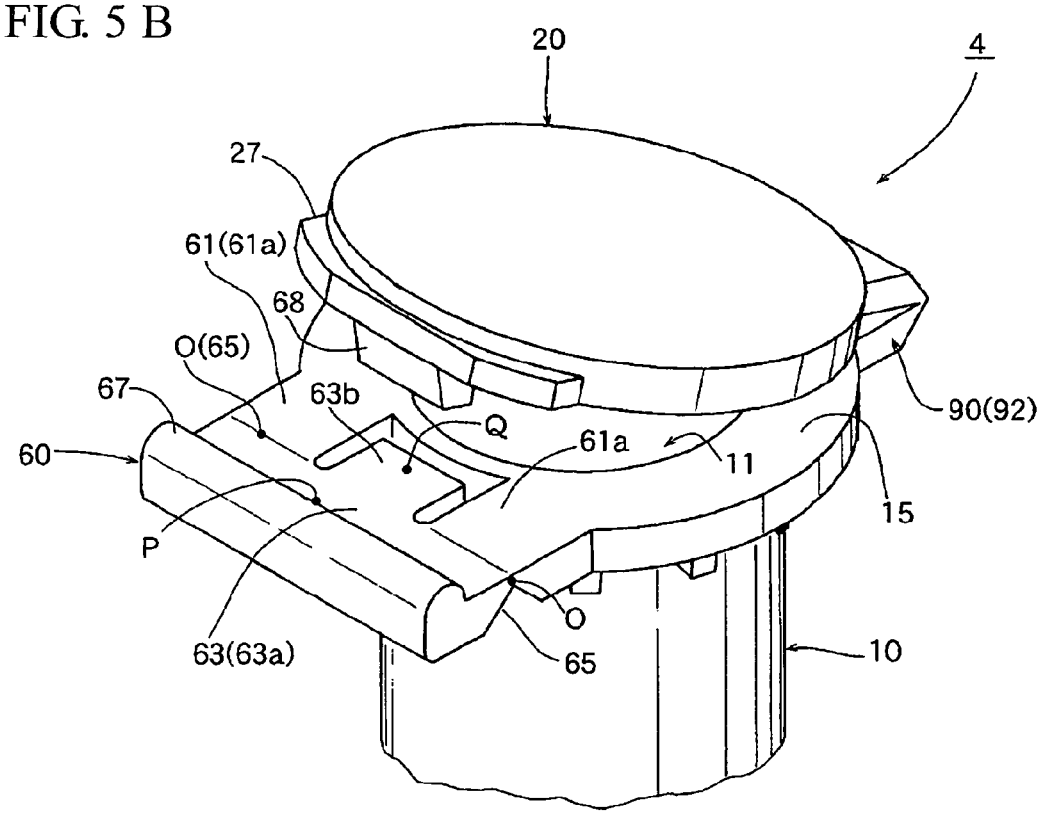
FIG. 5(B) shows a perspective view of the lid portion being closed.
Figure 6:
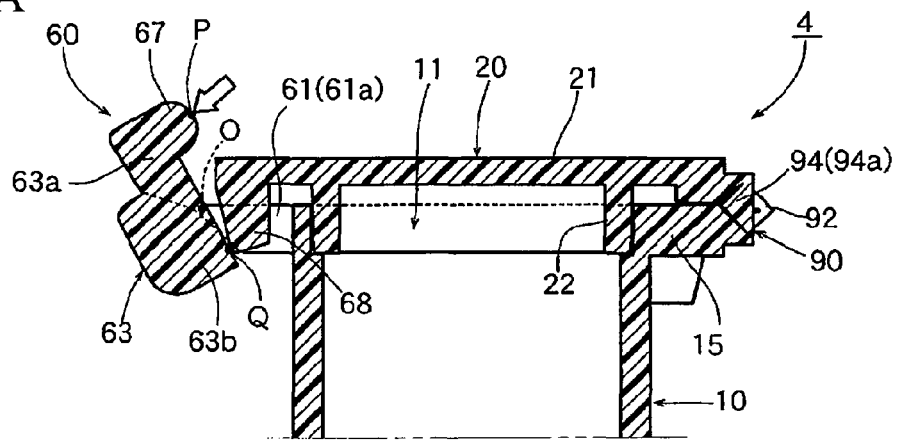
FIGS. 6(A), (B), and (C) show cross sections of the container with a lid according to the fourth embodiment, illustrating the lid portion as it is opened from a closed state in stages.
Figure 6:
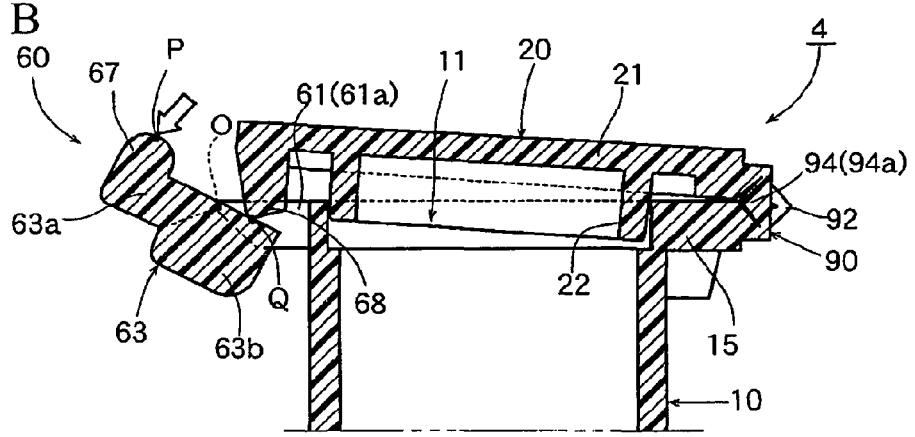
Figure 6:
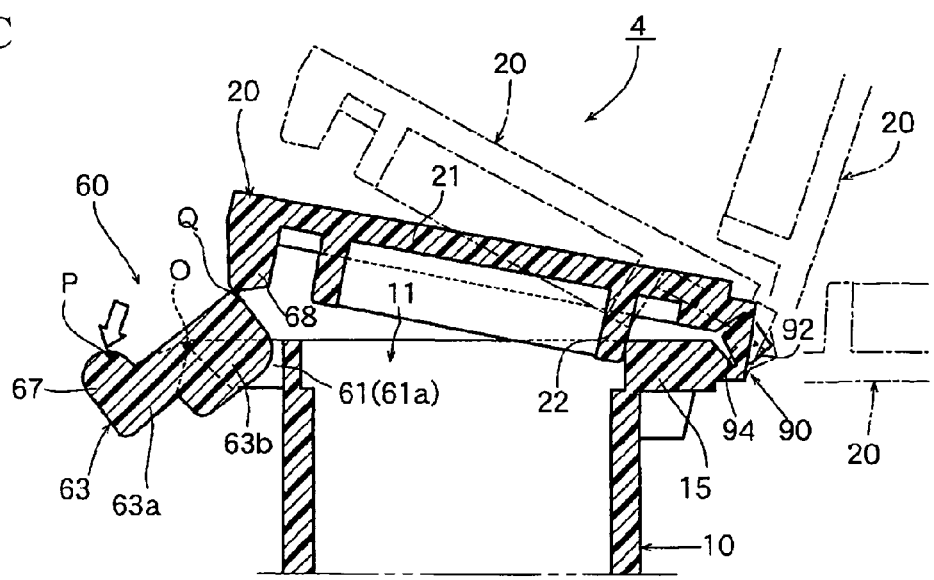

FIG. 5 shows a fourth embodiment of the container with a lid according to the invention. FIG. 5(A) shows a perspective view where the lid portion is open, and FIG. 5(B) shows a perspective view where the lid portion is being closed. FIGS. 6(A), (B), and (C) show cross sections of the container with a lid of the fourth embodiment, illustrating, in steps, how the lid portion is opened from the closed state.

The container with a lid 1 according to the present embodiment is similar to the container with a lid 1 according to the first embodiment, with the only difference lying in the structure of the lever mechanism portion. Since the other portions (container portion 10, lid portion 20, and so on) are substantially identical, attention is focused on the lever mechanism portion 50 in the following description.

The lever mechanism portion 60 of the container with a lid 4 according to the present embodiment includes a lever portion 63 having a force-applied point portion P which is pressed by a finger and an action point portion Q that is pressed against a lever swinging convex portion 68 protruding on the lower surface of the protruding nail portion 27 at the external periphery of the lid 20 in the closed state. It also includes a support portion 61 for supporting the lever portion 63 via a fulcrum O in a freely swinging manner.

The support portion 61 includes a pair of left and right support piece portions 61a and 61a that are continuous with the flange portion 15 and that protrude in a direction along the plane of the opening of the container portion 10 (radially outwardly). Between these support piece portions 61a and 61a, a lever portion 63 having a portion that is T-shaped in a plan view is disposed. The tip of each of the support piece portions 61a, 61a is connected to (the left and right sides of) a portion 63a of the lever portion 63 toward the force-applied point 63, via a thin-walled portion 65 that constitutes the fulcrum O and that has flexibility and appropriate resilience. The thin-walled portion 65 is formed with a groove with a triangular cross section on the internal peripheral surface thereof. The lever swinging convex portion 68 is adapted to press the action-point-side portion 63b of the lever portion 63 downward when the lid portion 20 is closed. Further, a finger-pressed convex portion 67 with a half-moon shaped cross section, which is to be pressed with a finger, is provided at the force-applied point P portion of the lever portion 63.

Thus, the lever mechanism portion 60 according to the present embodiment is of a rotating type wherein the fulcrum O exists between the force-applied point P and the action point Q in the lever portion 63.

The lid portion 20 is integrally connected to the container portion 10 via a lid hinge portion 90 composed of plate members having a thin-walled portion, in a freely swinging manner. As will be readily seen from FIG. 5, the lid hinge portion 90 composed of plate members consists of a left/right pair of first plate hinge portions 92, 92 having appropriate resilience and formed side by side with a predetermined interval therebetween, and a second plate hinge portion 94 disposed between the first plate hinge portions 92, 92. Each of the first plate hinge portions 92 has a thin-walled bending portion 92a formed as a groove near the center of the lower surface thereof. The second plate hinge portion 94 has a convex, ridge-shaped portion 94a formed near the center thereof. On either side of the ridge-shaped portion 94a, thin-walled bending portions 94b, 94b are formed.

The individual members of the container with a lid 1 according to the present embodiment, namely, the container portion 10, the lid portion 20, the flange portion 15, the lever mechanism portion 60, the hinge portion 90, the protruding nail portion 27, and the lever swinging convex portion 68, for example, are all integrally formed from the same material (synthetic resin material such as polypropylene).

In the thus structured container with a lid 1, when opening the lid portion 20 from the closed state shown in FIG. 6(A), the container portion 10 is held with one hand, and the finger-pressed convex portion 67 (force-applied point P) of the lever portion 63 of the lever mechanism portion 60 is pressed diagonally downward with the thumb of the one hand. As a result, as shown in FIGS. 6(B) and (C), the finger-pressed convex portion 67 (force-applied-point side portion 63a) of the lever portion 63 is pushed downward via the fulcrum O at the (center of) thin-walled portion 65 (by the elastic deformation of the thin-walled portion 65). At the same time, the action point Q on the upper surface of the other end of the lever portion 63 (action-point-side portion 63b) is pressed against the lower surface of the lever swinging convex portion 68 and raises the same, whereby the lid portion 20 is opened. Since the thin-walled portion 65 has appropriate resilience, the lever portion 63 returns to its original position (horizontal position) as the user releases his or her from the lever portion 63 after the lid portion 20 is opened. Thus, the lever portion does not pose an obstacle when closing the lid portion 20, for example.

When opening the lid portion 20, a large force is required initially, but it can be easily fully opened once it is moved even a little in the opening direction. Thus, the same operational effect as that of the first embodiment can be obtained.

In accordance with the container with a lid 4 of the present embodiment, because the lid portion 20 is provided with the lever swinging convex portion 68, it is possible to cause the force-applied-point side portion 63a of the lever portion 63 to swing upward beyond the fulcrum O. As a result, the length that the lever portion protrudes laterally (in the horizontal direction) can be reduced while a desired leverage ratio is maintained, as compared with the container with a lid 1, 2, or 3 according to the first, second, or third embodiment when the lid portion 20 is closed. Thus, the space occupied by the container with a lid (particularly in a plan view) can be reduced.

Because of the finger-pressed convex portion 67 provided at the force-applied-point portion P of the lever portion 63 that is pressed by a finger, the operation for opening the lid portion 20 using the lever mechanism portion 60 can be even more facilitated.

Because the lever mechanism portion 30 has a simple structure where it is integrally formed with the other members, the container with a lid 4 as a whole can be manufactured at approximately the same cost as is conventional.

When the lid portion 20 is closed from the horizontally open position as shown by phantom lines in FIG. 6(C), as the lid portion 20 is swung by nearly 90°, the lid portion 20 automatically falls in the closing direction (it swings to the left by approximately 60° to 90°) due to the operation of the lid hinge portion 90. Thus, the operation for closing the lid portion 20 can be performed easily.

Fifth Embodiment

Figure 7:
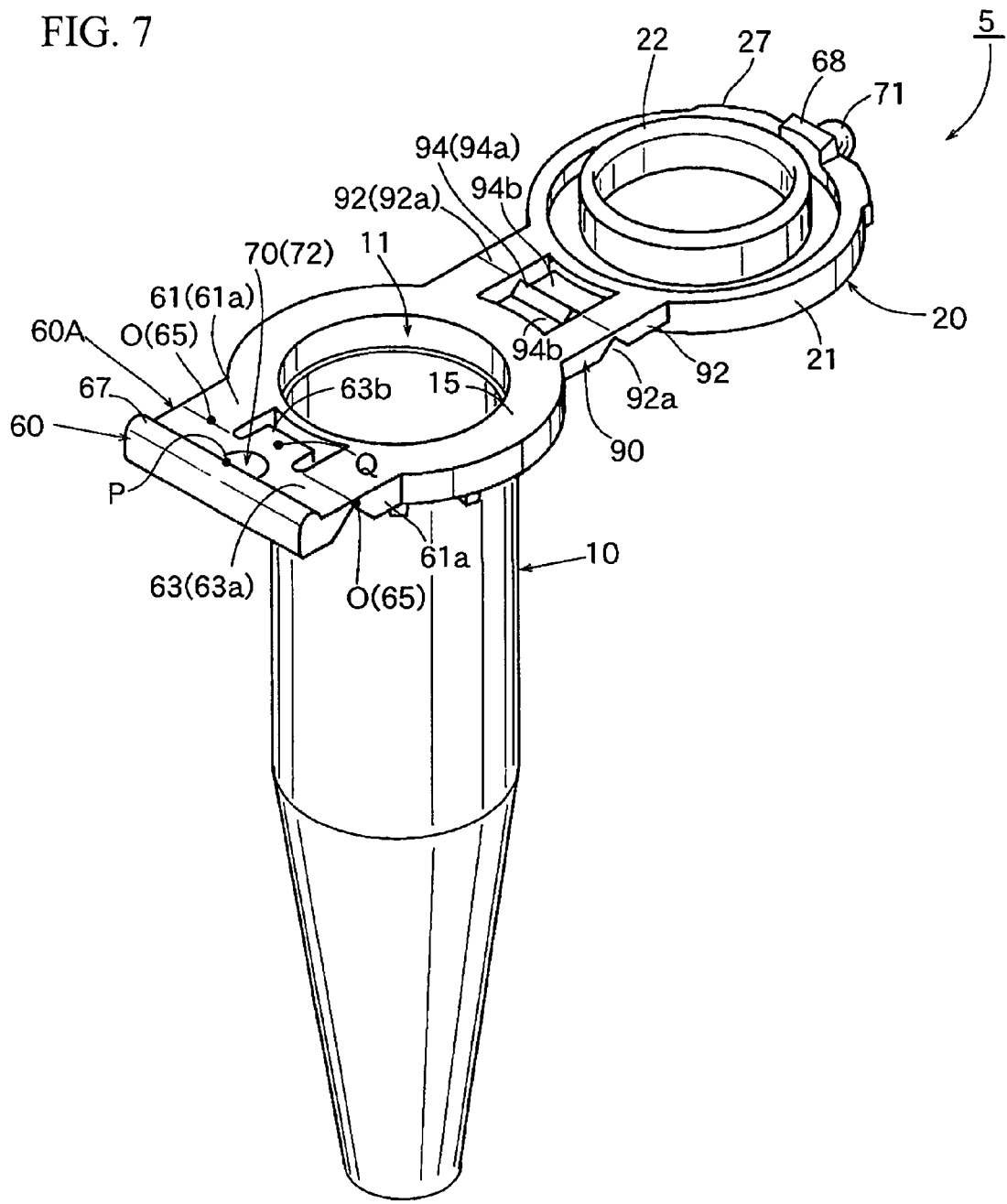
FIG. 7 shows a perspective view of a container with a lid according to a fifth embodiment of the invention, in which the lid portion is opened.
Figure 8A:
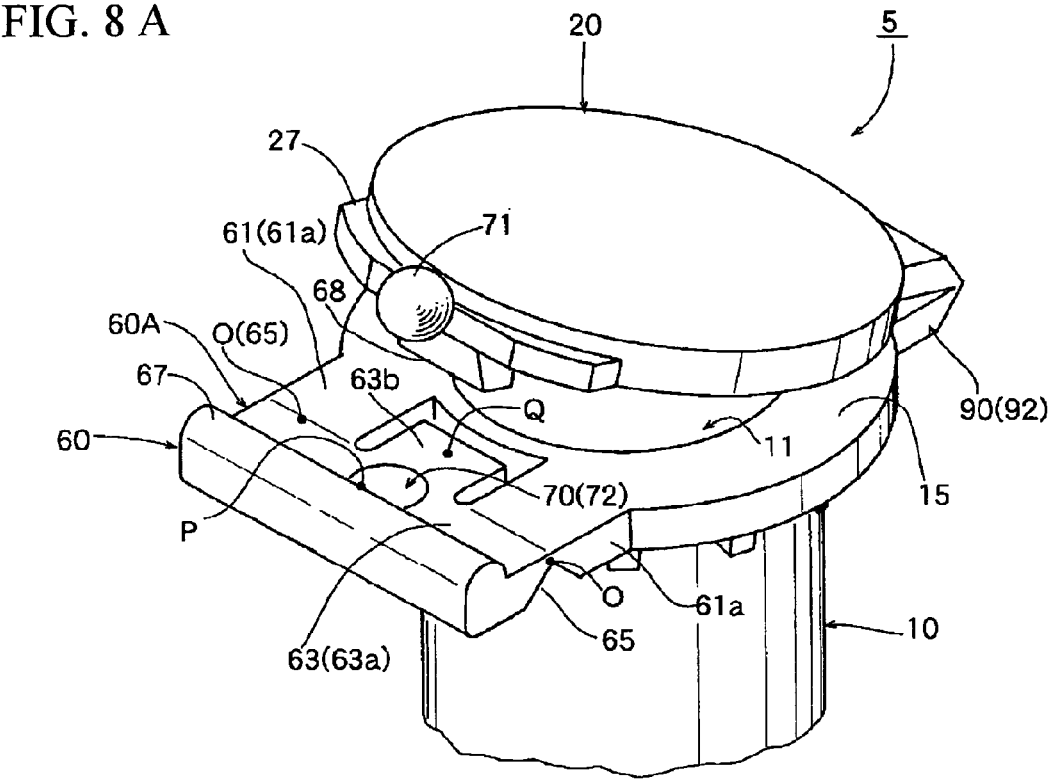
FIG. 8(A) shows a perspective view of the container with a lid according to the fifth embodiment in which the lid portion is being closed.
Figure 8B:
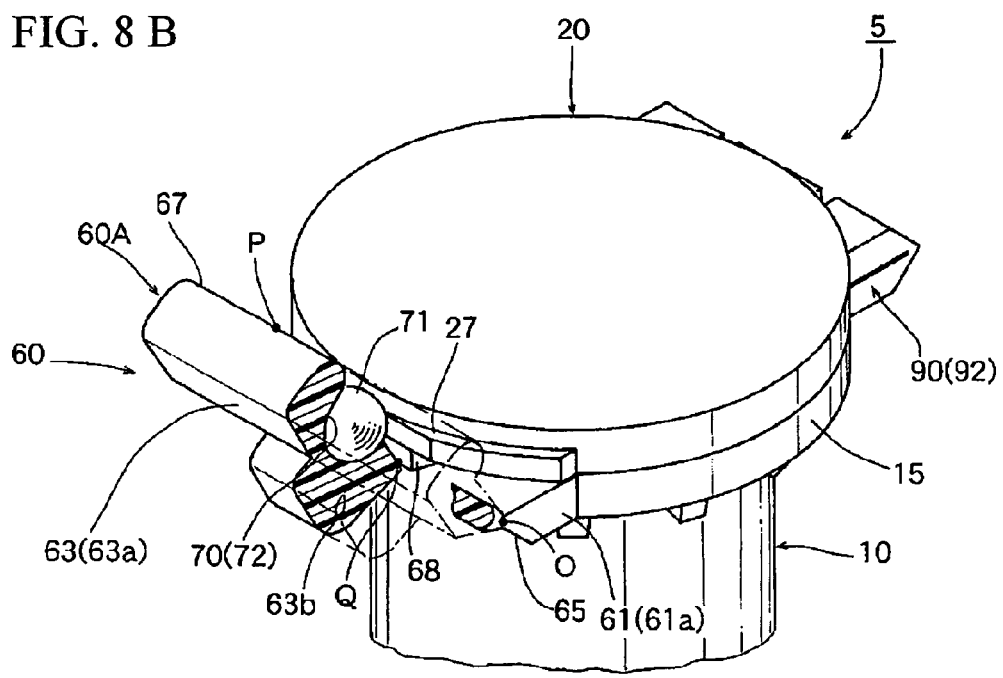
FIG. 8(B) shows a partially broken perspective view showing a closed lid portion.
Figure 9:
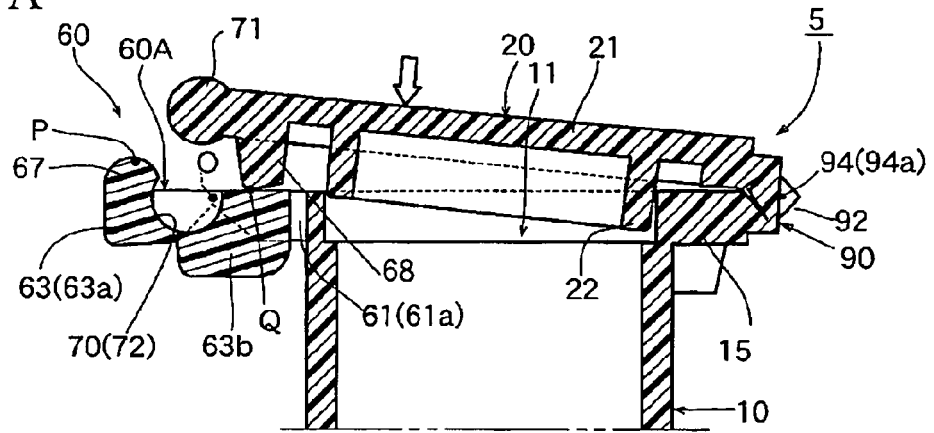
FIGS. 9(A), (B), and (C) show cross sections of the container with a lid according to the fifth embodiment, showing the lid portion as it is closed from an open state in stages.
Figure 9:
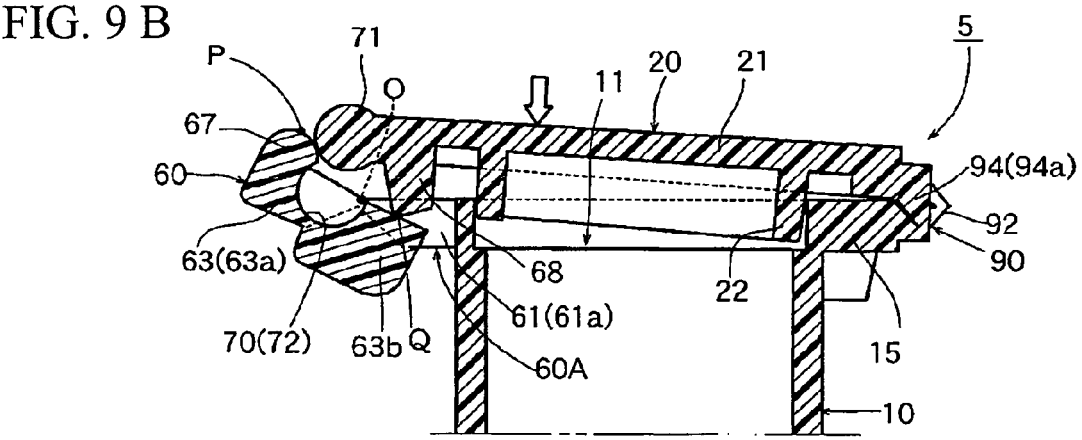
Figure 9:
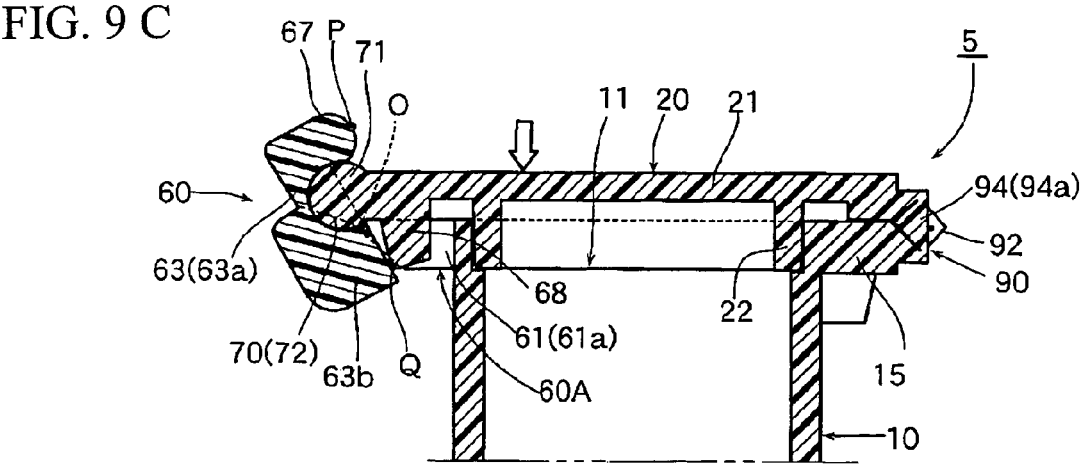

FIGS. 7, 8, and 9 show a fifth embodiment of the container with a lid of the invention. FIG. 7 is a perspective view showing the lid portion opened. FIG. 8(A) is a perspective view with the lid portion closed, and FIG. 8(B) is a partially broken perspective view showing how the lid portion is closed from the state (A). FIGS. 9(A), (B), and (C) are cross sections showing in steps how the lid portion is closed from the open position.

The container with a lid 4 according to the fifth embodiment is similar to the container with a lid 4 according to the fourth embodiment with the exception that a lock mechanism portion 70 that is operatively linked with the lever mechanism portion 60 is added. Therefore, in the following description, attention is focused on the lever mechanism portion 60 and the lock mechanism portion 70.

Namely, in the container with a lid 5 according to the fifth embodiment, the lever mechanism portion 60 includes a support portion 61 and a lever portion 63 with the same structures as those of the fourth embodiment. The lever portion 63 is connected to (the support piece portions 61a, 61a of) the support portion 61 via a thin-walled portion 65 constituting the fulcrum O, thereby forming a leverage/locking hinge portion 60A. The lock mechanism portion 70 consists of a first locking portion (spherical locking portion) 71 integrally formed with the lid portion 20 so as to protrude from near the protruding nail portion 27 radially outwardly, and a second locking portion (sphere-locking concave portion) 72 comprised of a concave portion having a spherical surface provided at the center of the force-applied-point side portion 63a of the lever portion 63 of the leverage/locking hinge portion 60A, in which concave portion the spherical locking portion 71 is adapted to be fitted. The sphere-locking concave portion 72 is formed such that the finger-pressed convex portion 67 is partially gouged. In this case, the spherical locking portion 71 and the sphere-locking concave portion 72 are adapted such that, when the lid portion 20 is closed, they become resiliently deformed (particularly the rim of the opening of the sphere-locking concave portion 72 is elastically expanded), and approximately two thirds of the volume of each is fitted within each other (see FIG. 9(B) to (C)).

Thus, in the container with a lid 5 according to the fifth embodiment having the lever mechanism portion 60 and the lock mechanism portion 70, in order to open the lid portion 20, the container portion 10 is held with one hand, as in the fourth embodiment, and one end of the lever portion 63 of the lever mechanism portion 60 (force-applied point P) is pressed with the thumb of the one hand. As a result, the pressing force is increased in accordance with the leverage ratio when it acts on the lid portion 20. Thus, the lid portion 20 can be easily opened with one hand without putting too much burden on the fingers even if it is closed too tightly. In this case, the lever mechanism portion 60 are operatively linked with the lock mechanism portion 70. Specifically, as the lid portion 20 is opened by the lever mechanism portion 60 (from (C) to (B) to (C) in FIG. 9), the locking of the lid portion 20 by the lock mechanism portion 70 is automatically released.

In order to lock the lid portion 20, the container portion is held with one hand, for example, and the lid portion is closed with the one hand (or the other hand) ((A) to (B) to (C) in FIG. 9). In response, namely, as the lid portion 20 is closed, the lever portion 63 (one side of the leverage/locking hinge portion 60A=force-applied-point side portion 63a) of the lever mechanism portion 60 is swung in the opposite direction from when the lid is opened, whereby the spherical locking portion 71 and the sphere-locking concave portion 72 are elastically deformed and fitted with each other. As a result, the lid portion 20 is automatically locked, so that the inadvertent opening of the lid portion by an increase in the internal pressure or the like can be prevented.

Thus, in accordance with the container with a lid 5 including the lever mechanism portion 60 and the lock mechanism portion 70, the locking and unlocking operations can be automatically performed in operative linkage with the closing operation of the lid portion 20 and the opening operation of the lid portion 20 by the lever mechanism portion 60. Thus, as compared with conventional examples in which the lid portion is locked with a separate clip or the like, the locking and unlocking operations can be extremely simplified and performed with reliability.

In addition, because the lever mechanism portion 60 and the lock mechanism portion 70 have relatively simple structures so that they can be integrally formed with the other members, the container with a lid as a whole can be manufactured at approximately the same cost as is conventional.

Sixth Embodiment

Figure 10:
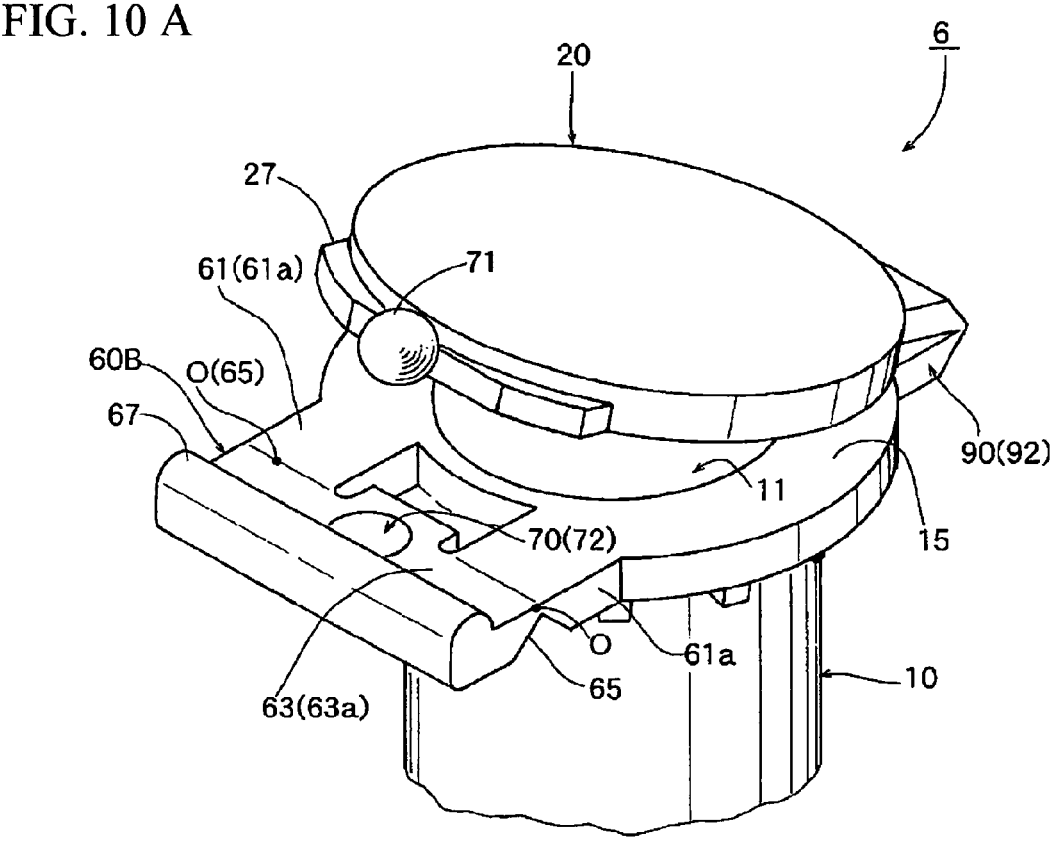
FIG. 10 shows a container with a lid according to a sixth embodiment of the invention.
Figure 10:
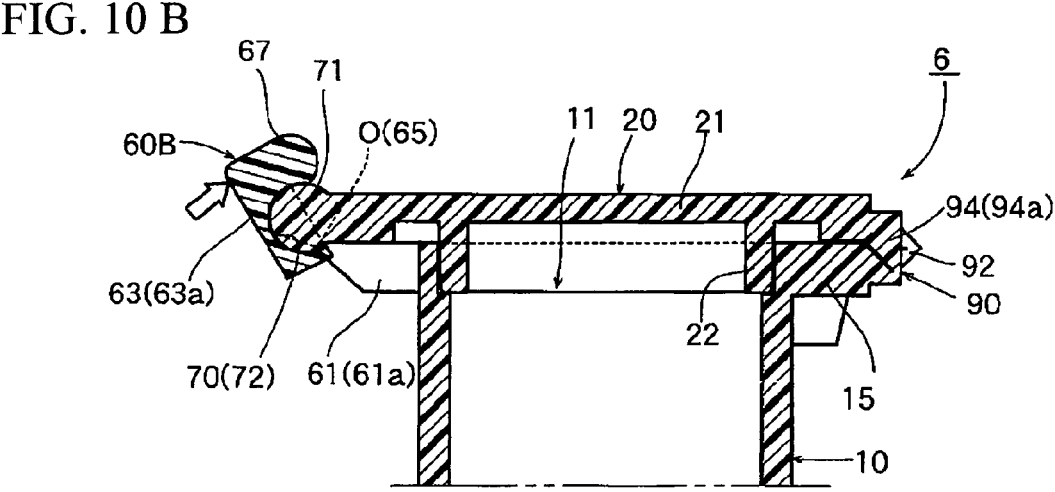

FIG. 10 shows a sixth embodiment of the container with a lid of the invention. FIG. 10(A) is a perspective view showing the lid portion opened, and FIG. 10(B) is a perspective view showing the lid portion closed.

The container with a lid 6 according to the sixth embodiment is provided only with the lock mechanism portion 70. Therefore, parts corresponding to those of the container with a lid 5 according to the fifth embodiment will be referred to with the same numerals and redundant explanations will be dispensed with.

In the container with a lid 6 of the present embodiment, the lock mechanism portion 70 is integrally provided. When locking the lid portion 20 as closed, the container portion 10 is held with one hand, for example, and one side of the locking hinge portion 60B where the sphere-locking concave portion 72 is provided is swung toward the spherical locking portion 71 with the one hand (or the fingers of the other hand). As a result, the spherical locking portion 71 and the sphere-locking concave portion 72 are resiliently deformed and become fitted with each other, whereby the lid portion 20 is locked and the lid portion can be prevented from being inadvertently opened due to an increase in internal pressure or the like. Furthermore, in order to unlock the lock mechanism portion 70 when opening the lid portion 20, it is only necessary to swing one side of the locking hinge portion 60B, where the sphere-locking concave portion 72 is provided, in the opposite direction from when locking, namely, away from the spherical locking portion 71.

Thus, in the container with a lid 6 according to the present embodiment having the lock mechanism portion 70, as compared with conventional examples where the lid portion 20 is locked with a separate clip or the like, the locking and unlocking operations can be performed easily.

Furthermore, because the lock mechanism portion 70 has a simple structure such that it can be integrally formed with the other members, the container with a lid as a whole can be manufactured at approximately the same cost as is conventional.

Seventh Embodiment

Figure 11:
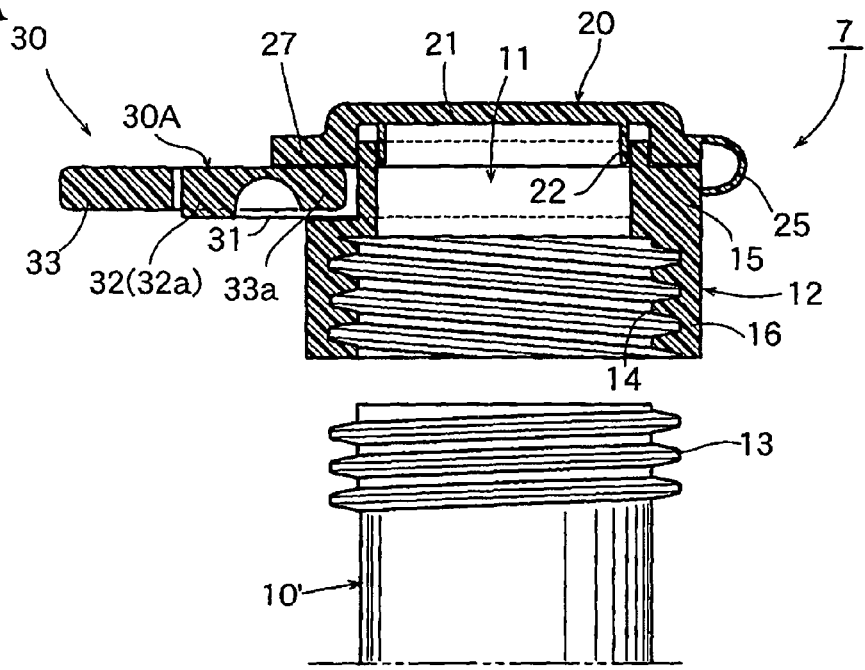
FIG. 11 shows a container with a lid according to a seventh embodiment of the invention.
Figure 11:
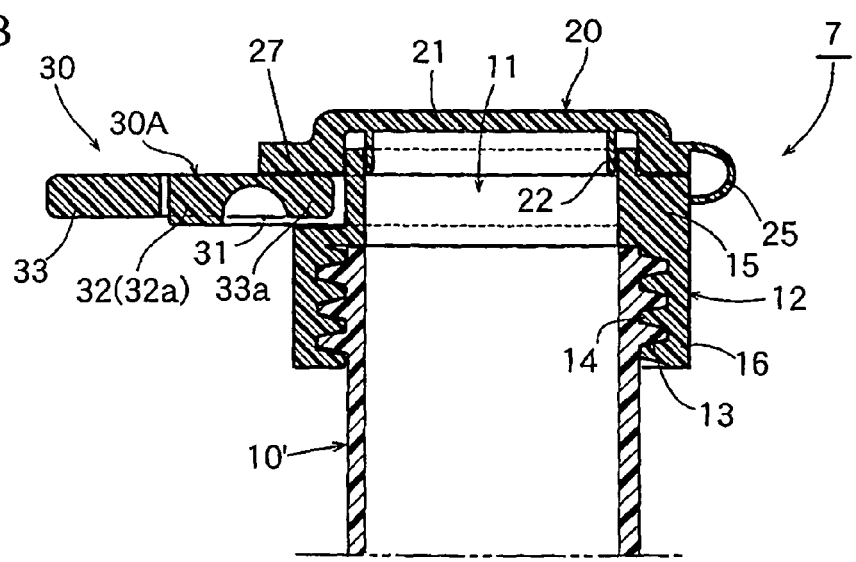

FIG. 11 shows a seventh embodiment of the container with a lid of the invention. The container with a lid 7 of the seventh embodiment is similar to the container with a lid 1 according to the first embodiment with the exception that the container portion 10 is separated from the other portions (flange portion 15, hinge portion 25, lid portion 20, and lever mechanism portion 30 of which the upper portion of the container with a lid 1 is composed). In the present embodiment, the portions other than the container portion can be detachably attached to the container portion.

Specifically, in the container with a lid 7 of the present embodiment, as shown in FIGS. 11(A) and (B), the lid portion 20, the hinge portion 25, the flange portion 15, and the lever mechanism portion 30, which are substantially identically structured to those of the first embodiment, are constructed in the form of a detachable lid member 12 that is separate from the container portion 10'. The detachable lid member 12 has a flange portion 15 from which a cylinder portion 16 extends downward. On the internal periphery of the cylinder portion 16, a female screw portion 14 is formed which is threadedly engaged with a male screw portion 13 formed on the external periphery at the top of the container portion 10'. The members of which the detachable lid member 12 is composed, namely, the lid portion 20, the hinge portion 25, the flange portion 15, the lever mechanism portion 30, and the cylinder portion 16 having the female screw portion 14 are integrally formed from the same synthetic resin material. By threading the female screw portion 14 of the detachable lid member 12 into the male screw portion 13 of the container portion 10' (until the lower-end surface of the flange portion 15 is abutted on the upper-end surface of the container portion 10'), the detachable lid member 12 can be attached to the container portion 10'. Conversely, by releasing the threaded engagement, the detachable lid member can be separated from the container portion 10'.

By thus constructing the container with a lid 7 with the container portion 10' and the detachable lid member 12 that can be detachably attached to each other, it becomes possible to produce the detachable lid member 12 and the container portion 10' with different materials, so that the degree of freedom in the choice of material can be increased.

In the foregoing seventh embodiment, the detachable lid member is composed of the same lid portion 20, hinge portion 25, flange portion 15, and lever mechanism portion 30 as those of the first embodiment. However, this is merely an example, and the structures according to the second to the sixth embodiments (having lever mechanism portions and/or lock mechanism portions or the like with different structures) may also be used. Thus, by preparing in advance a plurality of kinds of detachable lid members (having a female screw portion 14 that can be threadedly engaged with the male screw portion 13) with different structures in the lever mechanism portion or the lock mechanism portion or the like, and that can be detachably attached to the container portion 10', one that is most suitable in view of the type of the sample or the environment in which it is stored can be selected from among them. Because the container portion 10' can be commonly used, an increase in product value and cost reduction can be achieved as compared with a case where a plurality of types of containers with a lid where the container portion and the other portions are integrally formed.

While in the foregoing embodiment the container portion 10' and the detachable lid member 12 are both provided with the screw portions 13 and 14 for the detachment/attachment purposes, this is merely an example and other means may be employed for allowing the detachable lid member to be detachably attached to the container portion. For example, the two may be detachably fitted with each other by means of their respective resilience.

The invention claimed is:

1. A container with a lid comprising:
   a container portion having an opening portion for loading and unloading contents;
   a lid portion that can be detachably fitted in said opening portion so as to close the lid portion, the lid portion including a periphery portion;
   a lever mechanism portion that includes a lever mechanism for opening said lid portion when said opening portion is closed thereby; and
   a lock mechanism portion so as to lock said lid portion when said opening portion is closed thereby, wherein the lock mechanism portion includes a first locking portion provided on the lid portion, a second locking portion integrally formed with the container portion, and a locking hinge portion which is connected between the second locking portion and the container portion, the first locking portion and the second locking portion being operatively positioned such that the second locking portion lockingly engages the first locking portion by elastically deforming in response to the lid portion closing which swings the second locking portion along the locking hinge portion to engage the first locking portion, and the lever mechanism is integrally connected to the container portion and includes a force-applied point portion integrally formed with the second locking portion and on which finger pressure is applied and an action point portion that is positioned to press against the periphery portion of said lid portion, the locking hinge portion further being formed to provide a fulcrum between the force-applied point portion and the action point portion such that the action point portion opens the lid portion when the action point portion presses against the periphery portion of the lid portion in response to finger pressure being applied to the force-applied point portion.

2. The container with a lid according to claim 1, wherein said lever mechanism portion and said lock mechanism portion are operatively linked with each other.

3. The container with a lid according to claim 1, wherein, in response to an operation to close said lid portion, said lid portion is automatically locked by said lock mechanism portion, and wherein, in response to an operation to open said lid portion by said lever mechanism portion, the locking of said lid portion by said lock mechanism portion is automatically released.

4. The container with a lid according to claim 1, wherein said first locking portion of said lock mechanism portion is spherical in shape, wherein said second locking portion comprises a concave portion having a spherical surface in which said first locking portion can be fitted, and wherein at least one of said first locking portion and said second locking portion engages the other by elastically deforming upon closing of said lid portion.

5. The container with a lid according to claim 1, wherein said lid portion is provided with a lever swinging convex portion that presses the action point portion of said lever mechanism downward when said lid portion is closed.

6. The container with a lid according to claim 1, wherein said lid portion is connected with said container portion via a lid hinge portion in a freely swinging manner.

7. The container with a lid according to claim 1, wherein said container portion is cylindrical in shape at least in an upper portion thereof and is of such a size that it can be held with one hand.

8. The container with a lid according to claim 1, wherein said container portion comprises a container that is referred to as a sample tube that is used for the storage of a sample.

9. The container with a lid according to claim 1, wherein the individual portions are formed of the same material.

10. The container with a lid according to claim 1, wherein the individual portions are made of one or a plurality of kinds of materials from synthetic resin, metal, glass, ceramic, and a composite material thereof.

11. A container with a lid comprising:
    a container portion having an opening portion for loading and unloading contents;
    a lid portion that can be detachably fitted in said opening portion so as to close the lid portion, the lid portion including a periphery portion; and
    a lever mechanism portion for opening said lid portion when said opening portion is closed thereby, wherein said lever mechanism portion is integrally connected to the container portion and includes an action point portion detached from the periphery portion and a force-applied point portion on which finger pressure is applied to pivot the action point portion to move relative to the container portion and press against the periphery portion of said lid portion, and a fulcrum portion operatively positioned to provide a fulcrum between the force-applied point portion and the action point portion such that the action point portion is configured to open the lid portion by applying finger pressure to the force-applied portion to pivot the action point portion to move relative to the container portion and press against the periphery portion of the lid portion,
    wherein a lever portion and a support portion of said lever mechanism portion are continuous via a thin-walled portion that is flexible and that constitutes said fulcrum portion.

12. The container with a lid according to claim 11, wherein said thin-walled portion comprises a groove having a circular or triangular cross section on an internal surface of the groove.

13. The container with a lid according to claim 11, wherein said lid portion includes a protruding nail portion against which the action point portion of a lever portion is pressed and that protrudes in a direction along a plane of the opening of said container portion.

14. The container with a lid according to claim 11, wherein said container portion is cylindrical in shape at least in an upper portion thereof and is of such a size that it can be held with one hand.

15. The container with a lid according to claim 11, wherein said container portion comprises a container that is referred to as a sample tube that is used for the storage of a sample.

16. The container with a lid according to claim 11, wherein the individual portions are formed of the same material.

17. The container with a lid according to claim 11, wherein the individual portions are made of one or a plurality of kinds of materials from synthetic resin, metal, glass, ceramic, and a composite material thereof.

18. The container with a lid according to claim 11, wherein said support portion of said lever mechanism portion includes a pair of left and right support piece portions protruding, with a predetermined interval provided therebetween, in a direction along the plane of the opening of said container portion, wherein said lever portion is disposed between said pair of support piece portions, and wherein said pair of support piece portions is connected to a force-applied-point side portion of said lever portion via the thin-walled portion that constitutes said fulcrum portion.

19. The container with a lid according to claim 18, wherein at least said thin-walled portion is resilient.

20. A container with a lid comprising:
a container portion having an opening portion for loading and unloading contents;
a lid portion that can be detachably fitted in said opening portion so as to close the lid portion, the lid portion including a periphery portion; and
a lever mechanism portion for opening said lid portion when said opening portion is closed thereby, wherein said lever mechanism portion is integrally connected to the container portion and includes an action point portion detached from the periphery portion and a force-applied point portion on which finger pressure is applied to pivot the action point portion to move relative to the container portion and press against the periphery portion of said lid portion, and a fulcrum portion operatively positioned to provide a fulcrum between the force-applied point portion and the action point portion such that the action point portion is configured to open the lid portion by applying finger pressure to the force-applied portion to pivot the action point portion to move relative to the container portion and press against the periphery portion of the lid portion,
wherein said lid portion includes a lever swinging convex portion that presses the action point portion of a lever portion downward when said lid portion is closed.

21. The container with a lid according to claim 20, wherein said container portion is cylindrical in shape at least in an upper portion thereof and is of such a size that it can be held with one hand.

22. The container with a lid according to claim 20, wherein said container portion comprises a container that is referred to as a sample tube that is used for the storage of a sample.

23. The container with a lid according to claim 20, wherein the individual portions are formed of the same material.

24. The container with a lid according to claim 20, wherein the individual portions are made of one or a plurality of kinds of materials from synthetic resin, metal, glass, ceramic, and a composite material thereof.

25. A container with a lid comprising:
a container portion having an opening portion for loading and unloading contents;
a lid portion that can be detachably fitted in said opening portion so as to close the lid portion, the lid portion including a periphery portion; and
a lever mechanism portion for opening said lid portion when said opening portion is closed thereby, wherein said lever mechanism portion is integrally connected to the container portion and includes an action point portion detached from the periphery portion and a force-applied point portion on which finger pressure is applied to pivot the action point portion to move relative to the container portion and press against the periphery portion of said lid portion, and a fulcrum portion operatively positioned to provide a fulcrum between the force-applied point portion and the action point portion such that the action point portion is configured to open the lid portion by applying finger pressure to the force-applied portion to pivot the action point portion to move relative to the container portion and press against the periphery portion of the lid portion,
wherein a finger-pressed convex portion that is pressed by a finger is provided at a force-applied point portion of a lever portion.

26. The container with a lid according to claim 25, wherein said lid portion includes a protruding nail portion against which the action point portion of a lever portion is pressed and that protrudes in a direction along a plane of the opening of said container portion.

27. The container with a lid according to claim 25, wherein said container portion is cylindrical in shape at least in an upper portion thereof and is of such a size that it can be held with one hand.

28. The container with a lid according to claim 25, wherein said container portion comprises a container that is referred to as a sample tube that is used for the storage of a sample.

29. The container with a lid according to claim 25, wherein the individual portions are formed of the same material.

30. The container with a lid according to claim 25, wherein the individual portions are made of one or a plurality of kinds of materials from synthetic resin, metal, glass, ceramic, and a composite material thereof.

31. A container with a lid comprising:
a container portion having an opening portion for loading and unloading contents;
a lid portion that can be detachably fitted in said opening portion so as to close the lid portion, the lid portion including a periphery portion; and
a lock mechanism portion integrally provided with said container portion so as to lock said lid portion when said opening portion is closed thereby, wherein said lock mechanism portion includes a first locking portion that is spherical in shape and provided on the lid portion, and a second locking portion provided on a locking hinge portion integrally formed with the container portion, said second locking portion comprising a concave portion having a spherical surface in which said first locking portion can be fitted, wherein closing the lid portion is configured to automatically lock the lid portion in the closed position with the lock mechanism portion by swinging the second locking portion along the locking hinge portion to engage the first locking portion such that the second locking portion lockingly engages the first locking portion by elastically deforming in response to the lid portion closing.

32. The container with a lid according to claim 31, wherein said lid portion is connected with said container portion via a lid hinge portion in a freely swinging manner.

33. The container with a lid according to claim 31, wherein said container portion is cylindrical in shape at least in an upper portion thereof and is of such a size that it can be held with one hand.

34. The container with a lid according to claim 31, wherein said container portion comprises a container that is referred to as a sample tube that is used for the storage of a sample.

35. The container with a lid according to claim 31, wherein the individual portions are formed of the same material.

36. The container with a lid according to claim 31, wherein the individual portions are made of one or a plurality of kinds of materials from synthetic resin, metal, glass, ceramic, and a composite material thereof.

37. A container with a lid comprising:
- a container portion having an opening portion for loading and unloading contents;
- a lid portion that can be detachably fitted in said opening portion so as to close the lid portion, wherein said lid portion includes a periphery portion and is connected with said container portion via a lid hinge portion in a freely swinging manner; and
- a lever mechanism portion for opening said lid portion when said opening portion is closed thereby, wherein said lever mechanism portion is integrally connected to the container portion and includes an action point portion detached from the periphery portion and a force-applied point portion on which finger pressure is applied to pivot the action point portion to move relative to the container portion and press against the periphery portion of said lid portion, and a fulcrum portion operatively positioned to provide a fulcrum between the force-applied point portion and the action point portion such that the action point portion is configured to open the lid portion by applying finger pressure to the force-applied portion to pivot the action point portion to move relative to the container portion and press against the periphery portion of the lid portion.

38. The container with a lid according to claim 37, wherein said lid portion includes a protruding nail portion against which the action point portion of a lever portion is pressed and that protrudes in a direction along a plane of the opening of said container portion.

39. The container with a lid according to claim 37, wherein said container portion is cylindrical in shape at least in an upper portion thereof and is of such a size that it can be held with one hand.

40. The container with a lid according to claim 37, wherein said container portion comprises a container that is referred to as a sample tube that is used for the storage of a sample.

41. The container with a lid according to claim 37, wherein the individual portions are formed of the same material.

42. The container with a lid according to claim 37, wherein the individual portions are made of one or a plurality of kinds of materials from synthetic resin, metal, glass, ceramic, and a composite material thereof.

43. The container with a lid according to claim 37, wherein said lid hinge portion comprises a flexible sheet or wire member, or a plate member having a thin-walled portion, any of which member is integrally formed with said lid portion and said container portion.

44. The container with a lid according to claim 43, wherein said lid hinge portion comprising said plate member is composed of a first plate hinge portion and a second plate hinge portion that are formed side by side, wherein said first plate hinge portion has a thin-walled bending portion formed near the center thereof, said thin-walled bending portion comprising a groove that opens downwardly, and wherein said second plate hinge portion has a ridge portion formed near the center thereof which protrudes upwardly, wherein said thin-walled bending portion is formed on the left and right sides of said ridge portion.

45. The container with a lid according to claim 43, wherein said lid hinge portion is resilient.

* * * * *